United States Patent
Okada

(10) Patent No.: US 9,078,666 B2
(45) Date of Patent: Jul. 14, 2015

(54) MEDICAL DEVICE

(75) Inventor: Tsutomu Okada, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 934 days.

(21) Appl. No.: 13/078,162

(22) Filed: Apr. 1, 2011

(65) Prior Publication Data

US 2011/0245827 A1    Oct. 6, 2011

Related U.S. Application Data

(60) Provisional application No. 61/320,372, filed on Apr. 2, 2010.

(51) Int. Cl.
| | |
|---|---|
| A61B 18/14 | (2006.01) |
| A61B 17/29 | (2006.01) |
| A61B 1/018 | (2006.01) |
| A61B 17/00 | (2006.01) |
| A61B 17/32 | (2006.01) |
| A61B 17/3205 | (2006.01) |
| A61B 17/28 | (2006.01) |
| A61B 18/18 | (2006.01) |

(52) U.S. Cl.
CPC .............. *A61B 18/1492* (2013.01); *A61B 17/29* (2013.01); *A61B 1/018* (2013.01); *A61B 17/00234* (2013.01); *A61B 17/28* (2013.01); *A61B 17/320016* (2013.01); *A61B 17/32056* (2013.01); *A61B 2017/0034* (2013.01); *A61B 2017/2905* (2013.01); *A61B 2017/2911* (2013.01); *A61B 2018/1407* (2013.01); *A61B 2018/1422* (2013.01); *A61B 2018/1475* (2013.01); *A61B 2018/1861* (2013.01)

(58) Field of Classification Search
CPC .............. A61B 1/18; A61B 17/00234; A61B 17/320016; A61B 19/2203; A61B 2017/0034; A61B 17/32056; A61B 17/28; A61B 18/1492; A61B 17/29; A61B 2018/1422; A61B 2018/1407; A61B 2017/2911; A61B 2018/1861; A61B 2017/2905; A61B 2018/1475

USPC .............. 606/32–52; 600/104–106, 110, 113, 600/114, 127, 131; 81/3.41, 3.44; 173/213

See application file for complete search history.

(56) References Cited

U.S. PATENT DOCUMENTS

| | | | |
|---|---|---|---|
| 6,419,679 B1 * | 7/2002 | Dhindsa | 606/127 |
| 2004/0167514 A1 * | 8/2004 | Okada | 606/45 |

FOREIGN PATENT DOCUMENTS

| | | |
|---|---|---|
| EP | 1709900 A1 * | 10/2006 |
| JP | 2004-261372 | 9/2004 |

*Primary Examiner* — Jaymi Della
*Assistant Examiner* — Eunhwa Kim
(74) *Attorney, Agent, or Firm* — Scully, Scott, Murphy & Presser, P.C.

(57) ABSTRACT

A medical device includes a treatment portion, a long cylindrical insertion portion, an operation portion and transmission portion. The insertion portion includes a regulation member provided while being projected from an inner wall surface of the insertion portion for regulating a length by which the treatment portion protrudes from the distal end of the insertion portion. The transmission portion includes an operation wire inserted in the insertion portion and has a distal end fixed to the treatment portion and an contacting member fixed to the operation wire and disposed at a position opposite to the treatment portion with respect to the regulation member. A rotating bearing member contacting the regulation member and the contacting member respectively and can rotate relative to at least any one of the regulation member and the contacting member around an axis of the operation wire is provided between the regulation member and the contacting member.

8 Claims, 16 Drawing Sheets

MEDICAL DEVICE

CROSS-REFERENCE TO RELATED APPLICATIONS

The present application is based upon and claims the benefit of priority from prior U.S. Provisional Application No. 61/320,372 filed on Apr. 2, 2010; the entire contents of which are incorporated herein by reference.

BACKGROUND OF THE INVENTION

1. Field of the Invention

The present invention relates to a medical device.

2. Description of Related Art

Hitherto, as a medical device performing treatment in a body cavity, a medical device is known which includes a cylindrical insertion portion inserted into the body cavity, a treatment portion protruding from the insertion portion and performing treatment for treatment target sites in the body cavity, and an operation portion operating the treatment portion outside the body.

As an example of such a medical device, Japanese Patent Unexamined Application, First Publication No. 2004-261372 discloses a treatment device for an endoscope including an operation wire in which a knife portion (treatment portion) for making an incision in body tissue is fixed to a distal end thereof, an insertion portion having a sheath in which the operation wire is inserted, and an operation portion provided at a proximal end of the insertion portion. In the treatment device for an endoscope disclosed in Japanese Patent Unexamined Application, First Publication No. 2004-261372, a cylindrical contacting member with a diameter larger than that of the operation wire is fixed to the operation wire, and a stopper member having a through-hole with approximately the same size as the external diameter of the operation wire which freely advances or retreats through the through-hole formed therein is fixed to the distal end of the insertion portion.

According to the treatment device for an endoscope, when the operation wire is pushed into the insertion portion, the operation wire cannot be further pushed into the insertion portion from the place where the contacting member contacts the stopper member. Therefore, it is possible to position the treatment portion at the position where the treatment portion protrudes from the distal end of the insertion portion.

SUMMARY OF THE INVENTION

According to a first aspect of the present invention, a medical device includes a treatment portion performing treatment in a body cavity; a long cylindrical insertion portion for guiding the treatment portion into the body cavity; an operation portion for operating the treatment portion; and a transmission portion transmitting a driving force to the treatment portion from the operation portion and performing treatment with respect to body tissue by protruding the treatment portion from a distal end of the insertion portion, wherein the insertion portion includes a regulation member provided while being projected from an inner wall surface of the insertion portion for regulating a length by which the treatment portion protrudes from the distal end of the insertion portion, the transmission portion includes an operation wire inserted in the insertion portion and having a distal end fixed to the treatment portion and an contacting member fixed to the operation wire and disposed at a position opposite to the treatment portion with respect to the regulation member, and a rotating bearing member which is provided between the regulation member and the contacting member. The rotating bearing member can contact the regulation member and the contacting member respectively and can rotate relative to at least any one of the regulation member and the contacting member around the axis of the operation wire.

According to a second aspect of the present invention, a medical device includes a treatment portion treating a target site; a supporting portion supporting the treatment portion at its distal end; and a treatment portion rotation-regulating member fixed to the distal end of the supporting portion and regulating the rotation of the treatment portion performed around the axial direction of the supporting portion.

BRIEF DESCRIPTION OF THE DRAWINGS

FIG. 2A is a cross sectional view taken along a line A2-A2 of FIG. 1B, and FIG. 2B is a cross sectional view taken along a line A3-A3 of FIG. 2A.

DETAILED DESCRIPTION OF THE INVENTION

First Embodiment

Figure 1A:
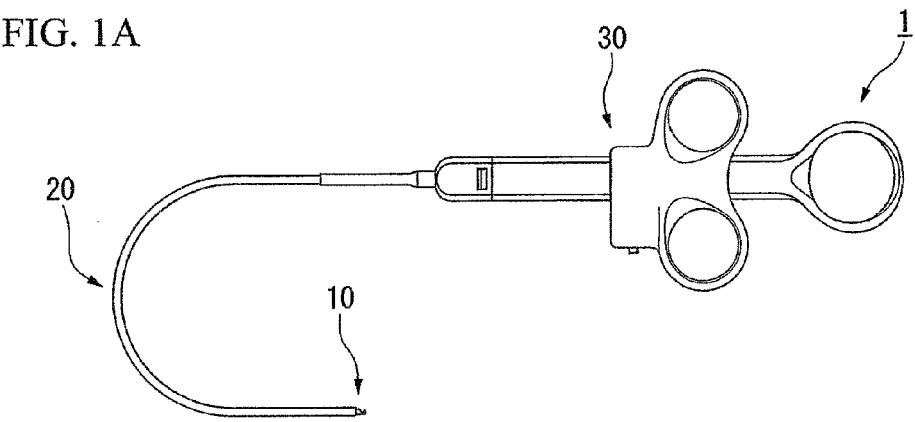
FIG. 1A is a plan view showing a medical device of a first embodiment of the present invention.

Hereinafter, a medical device 1 of a first embodiment of the present invention will be described with reference to FIGS. 1A to 6B. First, the configuration of the medical device 1 will be described with reference to FIGS. 1A to 2B. FIG. 1A is a plan view showing the medical device 1.

As shown in FIG. 1A, the medical device 1 includes a treatment portion 10 for performing treatment in a body cavity, an insertion portion 20 guiding the treatment portion 10 to a treatment target site in the body cavity, an operation portion 35 for operating the treatment portion 10 outside the body, and a transmission portion 30 transmitting a driving force to the treatment portion 10 from the operation portion 35.

The medical device 1 of the embodiment is an incisional instrument incising body tissue. Specifically, the medical device 1 is an incisional instrument for incising body tissue with cauterization by using the treatment portion 10, by applying high frequency current to the treatment portion 10 from the operation portion 35.

Figure 1B:
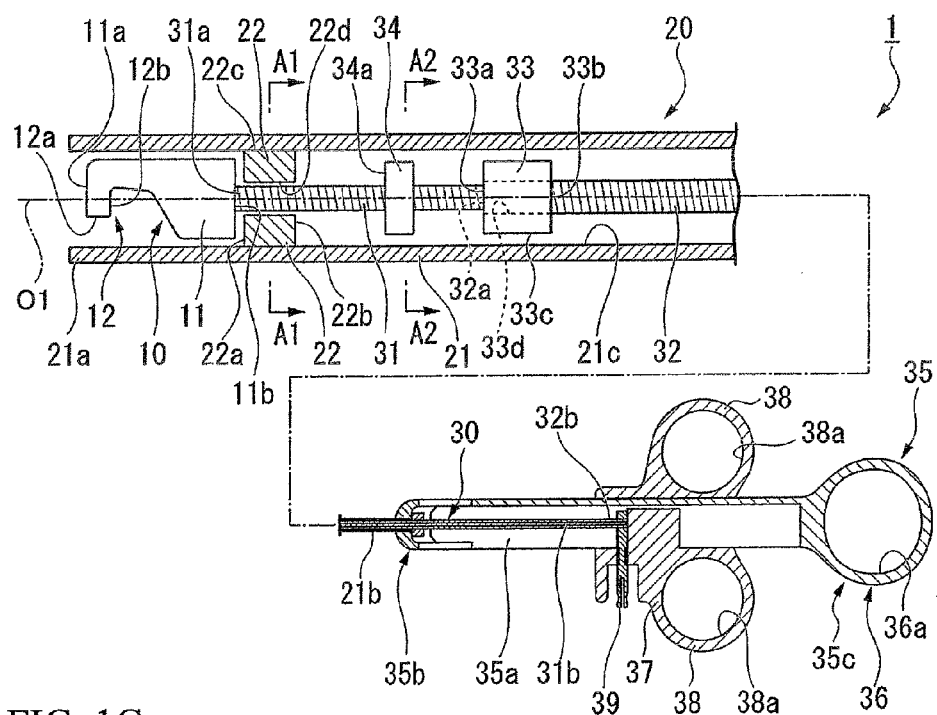
FIG. 1B is a partial cross sectional view showing a part of the configuration of the medical device.

FIG. 1B is a partial cross sectional view showing a part of the configuration of the medical device 1. As shown in FIG. 1B, the treatment portion 10 is a hook type treatment portion for incising the body tissue with cauterization while contacting the body tissue. The treatment portion 10 includes an incisional electrode body 11 having electric conductivity. In the incisional electrode body 11, a hook-like hook portion 12 is formed at a distal end 11a side. Also, a distal end 31a of an operation wire 31 (which will be described later in detail) is fixed to a proximal end 11b side of the incisional electrode body 11. The incisional electrode body 11 is so configured that it can advance or retreat in an axial direction of the insertion portion 20 in the insertion portion 20 through the operation wire 31.

The shape of the incisional electrode body 11 is a substantially plate-like shape and has such a size that it can be accommodated in the lumen of an outer tube 21 (described later) of the insertion portion 20. The shape of the incisional electrode body 11 is not limited to such a shape and may also be formed into appropriate shapes such as a cylindrical shape or a rectangular columnner shape.

The hook portion 12 provided at the distal end 11a side of the incisional electrode body 11 is formed into such a shape that it bends in a direction orthogonal to the direction in which the incisional electrode body 11 advances or retreats. In the hook portion 12, a hook tip portion 12a and an inner surface portion 12b are portions applying the high frequency current to the body tissue while being locked on the body tissue. Also, among the outer surfaces of the hook portion 12, by bringing the surface of the distal end 11a side opposite to the inner surface portion 12b into contact with the body tissue to apply the high frequency current, it is possible to incise the body tissue with cauterization.

A part of the outer surface of the hook portion 12 may be coated with an insulator. For example, the outer surface of the hook portion 12 other than the hook tip portion 12a and the inner surface portion 12b can be coated with an insulator such as a ceramic. In this case, even when the outer surface of the hook portion 12 other than the hook tip portion 12a and the inner surface portion 12b of the hook portion 12 contacts the body tissue, the portion of the body tissue other than the portion which contacts the hook tip portion 12a and the inner surface portion 12b is not incised. Accordingly, it is possible to incise the body tissue with favorable accuracy along a planned incision line. Further, the insulator may also be provided in the outer surface of the proximal end 11b side in the incisional electrode body 11, and in this case, it is also possible to further accurately incise the body tissue.

The insertion portion 20 includes the outer tube 21 in which the treatment portion 10 is accommodated in a distal end 21a side thereof and the operation portion 35 is connected to a proximal end 21b side thereof; and a cylindrical regulation member 22 fixed to the inner wall surface of the distal end 21a side of the outer tube 21.

The outer tube 21 is formed into a cylindrical shape having flexibility, and the size of the external diameter of the outer tube 21 is configured such that the outer tube 21 can freely advance or retreat in a treatment device channel according to the internal diameter of the treatment device channel of an endoscope, for example. Also, it is preferable that the length of the outer tube 21 is longer than the entire length of the treatment device channel of the endoscope. As a material for the outer tube 21, for example, a resin or the like can be used, and preferably, the material is an insulator having such an insulation property that it can insulate against the high frequency current passing through the operation wire 31.

Figure 1C:
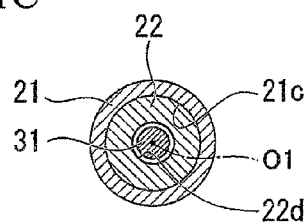
FIG. 1C is a cross sectional view taken along a line A1-A1 of FIG. 1B.

FIG. 1C is a cross sectional view taken along a line A1-A1 of FIG. 1B. As shown in FIG. 1C, the regulation member 22 is fixed to an inner circumferential surface 21c of the outer tube 21 by adhesion, for example. In the regulation member 22 fixed to the outer tube 21, a through-hole portion 22d coaxial with a central axis line O1 of the outer tube 21 is formed. The operation wire 31 is inserted in the through-hole portion 22d formed in the regulation member 22 so that the operation wire 31 can freely advance or retreat. The size of the external diameter of the regulation member 22 is the same as the internal diameter of the outer tube 21. The internal diameter (the diameter of the through-hole portion 22d) of the regulation member 22 is smaller than the internal diameter of the outer tube 21, and has such a size that the incisional electrode body 11 of the treatment portion 10 does not pass through the inside of the through-hole portion 22d.

As shown in FIG. 1B, at a distal end 22a of the regulation member 22, there is formed a surface orthogonal to the central axis line O1 of the outer tube 21. The proximal end 11b of the incisional electrode body 11 of the treatment portion 10 can contact the distal end 22a of the regulation member 22. Furthermore, at a proximal end 22b of the regulation member 22, there is also formed a surface orthogonal to the central axis line O1 of the outer tube 21. A distal end 34a of a rotating bearing member 34 described later can contact the proximal end 22b of the regulation member 22. As a material for the regulation member 22, an insulator similar to the material for the outer tube 21 is preferable, and for example, it is possible to use a resin as the material. Here, the regulation member 22 may be for example, formed of a conductive material such as a metal.

A transmission portion 30 includes the operation wire 31 disposed in the outer tube 21 and having the distal end 31a fixed to the incisional electrode body 11; an inner tube 32 disposed in the outer tube 21 and in which the operation wire 31 is inserted; and a rotating bearing member 34 rotatably mounted on the operation wire 31.

The operation wire 31 is welded to the proximal end 11b of the incisional electrode body 11 by laser welding, for example. The external diameter of the operation wire 31 is smaller than the internal diameter of the outer tube 21 and is almost the same as the internal diameter of the inner tube 32.

The shape of the operation wire 31 is a coil-like shape in which a wire rod is closely coiled. The operation wire 31 may also be formed into shapes other than the coil-like shape. For example, the operation wire 31 may also be formed into a linear shape extending in the axial direction of the outer tube 21.

As a material for the operation wire 31, a metallic wire rod that can carry the high frequency current is preferable; also, it is preferable for the material to have flexibility. In addition, it is preferable for the operation wire 31 to have such elasticity that the treatment portion 10 does not sag from the outer tube 21 when the operation wire 31 is drawn out from the distal end 21a of the outer tube 21. In this case, it is possible to easily handle the treatment portion 10. As a preferable material for the operation wire 31, stainless steel can be used.

The inner tube 32 is fixed to the operation wire 31 by laser welding, brazing, or the like, for example. The external diameter of the inner tube 32 is smaller than the internal diameter of the outer tube 21. The shape of the inner tube 32 is a coil-like shape in which a wire rod is closely coiled. Preferable examples of the shape of the inner tube 32 include a multilayered coil shape or a multi-thread coil shape that exhibits good transmission efficiency when transmitting torque around the rotation axis. Since the inner tube 32 has the coil-like shape, it has flexibility, and the torque produced when the inner tube 32 rotates around the axis by an operation body 35a can be easily transmitted to a distal end 32a side of the inner tube 32. Since the inner tube 32 and the operation wire 31 are fixed, it is possible to rotate the operation wire 31 around the rotation axis by rotating the inner tube 32 around the rotation axis; accordingly, it is possible to rotate the treatment portion 10 fixed to the operation wire 31 around the axis of the operation wire 31. Preferable examples of the material of the inner tube 32 include stainless steel.

In the distal end 32a of the inner tube 32, there is provided a cylindrical contacting member 33. An inner circumferential surface 33d of the contacting member 33 is fixed to the outer circumferential surface of the distal end 32a of the inner tube 32 by laser welding, brazing, swaging, or the like, for example. As a material for the contacting member 33, stainless steel can be used. At a distal end 33a of the contacting member 33, there is formed a surface orthogonal to the central axis line of the inner tube 32. The external diameter of the contacting member 33 is smaller than the internal diameter of the outer tube 21, and there is a gap between an outer circumferential surface 33c of the contacting member 33 and the inner circumferential surface 21c of the outer tube 21. This configuration is provided to make the contacting member 33 advance or retreat in the outer tube 21 even in a state where the outer tube 21 is curved. The length between the distal end 33a and a proximal end 33b of the contacting member 33 can be appropriately configured. In addition, if the length between the distal end 33a and the proximal end 33b of the contacting member 33 is made short, the hard portion in the insertion portion 20 can be reduced; accordingly, the insertion portion 20 can be easily inserted into the treatment device channel of the endoscope, or the like, for example.

Figure 2A:
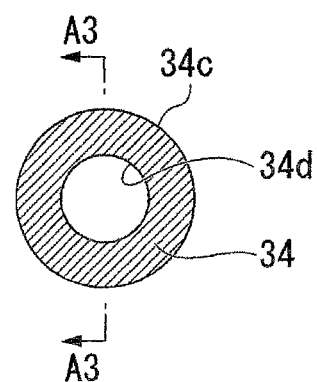
FIGS. 2A and 2B are views showing the configuration of a rotating bearing member in the medical device.
Figure 2B:
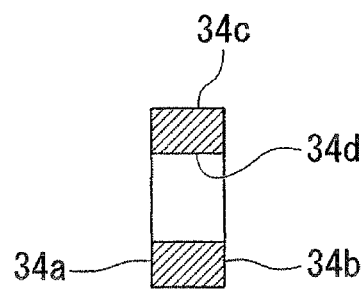

FIGS. 2A and 2B are views showing the configuration of the rotating bearing member 34. FIG. 2A is a cross sectional view taken along a line A2-A2 of FIG. 1B, and FIG. 2B is a cross sectional view taken along a line A3-A3 of FIG. 2A.

As shown in FIGS. 1B, 2A, and 2B, the rotating bearing member 34 is a cylindrical member in which a through-hole portion 34d respectively opened toward the distal end 34a and a proximal end 34b is formed. The operation wire 31 is inserted in the through-hole portion 34d, and the rotating bearing member 34 can freely rotate around the central axis line of the through-hole portion 34d with respect to the operation wire 31.

The length between the distal end 34a and the proximal end 34b of the rotating bearing member 34 can be appropriately configured. As a material for the rotating bearing member 34, a resin can be used. Particularly, it is preferable that the rotating bearing member 34 is formed of a material for which friction coefficients of the rotating bearing member 34 with the regulation member 22 and with the contacting member 33 are smaller than a friction coefficient between the regulation member 22 and the contacting member 33. Specifically, as a material for the rotating bearing member 34, it is possible to use polymers having an oxymethylene structure as a unit structure, such as polyacetal or polyoxymethylene (POM). Also, as a material for the rotating bearing member 34, it is also possible to use a silicone rubber, a fluororesin, and a metal such as stainless steel or the like. In addition, if the friction coefficient between the contacting member 33 and the rotating bearing member 34 and the friction coefficient between the rotating bearing member 34 and the regulation member 22 are such friction coefficients that the contacting member 33 and the regulation member 22 do not perform relative rotation when body tissue is incised by using the treatment portion 10, it is possible to stabilize the direction of a hook tip portion 12a of the hook portion 12 when the body tissue is incised, and thus is preferable.

The operation portion 35 is used for operating the treatment portion 10 through the operation wire 31. The operation portion 35 includes an operation body 35a to which a proximal end 31b of the operation wire 31 and a proximal end 32b of the inner tube 32 are fixed and the proximal end 21b of the outer tube 21 is connected.

The operation body 35a is formed into a substantially cylindrical shape in which a portion of the lateral wall is cut out. The outer tube 21 connected to the distal end of the operation body 35a freely rotates relative to the operation body 35a around the axis of the outer tube 21. At a proximal end 35c side of the operation body 35a, there is provided a finger-hooking portion 36 formed into a ring-like shape being projected outside the radial direction from the operation body 35a. The operation body 35a is also provided with a sliding member 37 interlockingly mounted on the outer surface of the operation body 35a so that the sliding member 37 is slidable in the axial direction.

In the finger-hooking portion 36, there is formed a through-hole portion 36a having a central axis line facing the direction orthogonal to the axis of the operation body 35a, and an operator using the medical device 1 inserts their thumb in the through-hole portion 36a.

In the sliding member 37, at two places in total of both sides of the operation body 35a as a center, there are formed finger-hooking portions 38 being projected outside the radial direction of the operation body 35a.

In each of the finger-hooking portions 38, there is formed a through-hole portion 38a having a central axis line parallel to the central axis line of the through-hole portion 36a. An operator using the medical device 1 inserts their index finger or middle finger in the through-hole portion 38a.

Furthermore, in the sliding member 37, there is formed a rod-like contact electrode portion 39 in which one end thereof is positioned in the operation body 35a, and the other end thereof extends outside the radial direction of the operation body 35a so as to be exposed outside.

The contact electrode portion 39 has electric conductivity, and the proximal end 31b of the operation wire 31 is fixed to one end side of the contact electrode portion 39 by laser welding, swaging, or the like, for example. The other end of the contact electrode portion 39 can be connected to a high frequency power-supply device (not shown). Accordingly, the high frequency current can pass between the contact electrode portion 39 and the operation wire 31.

Hereinafter the operation of the medical device 1 having the above-described configuration will be described.

Figure 3A:
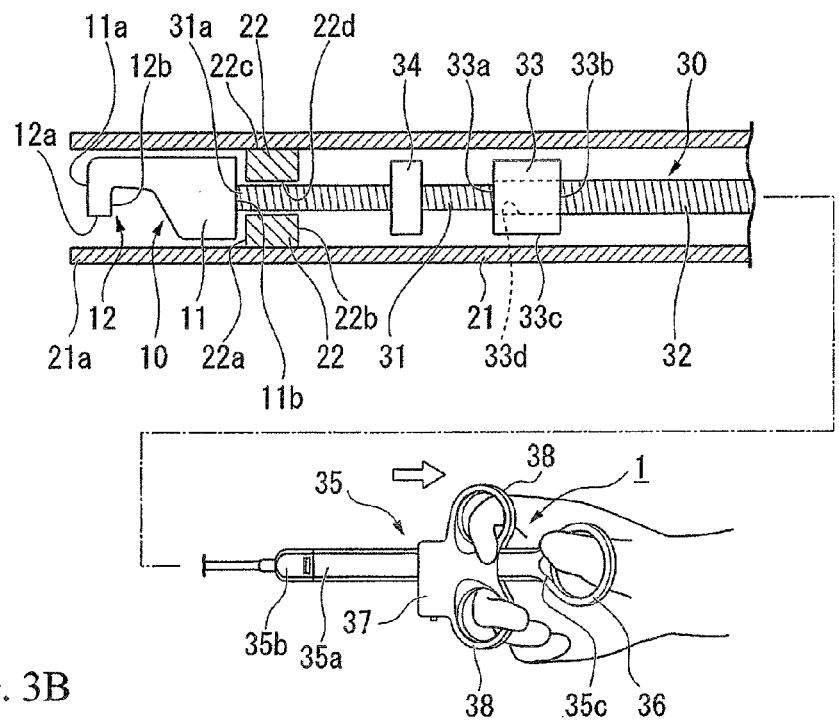
FIGS. 3A and 3B are illustrative views for describing the operation of the medical device.
Figure 3B:
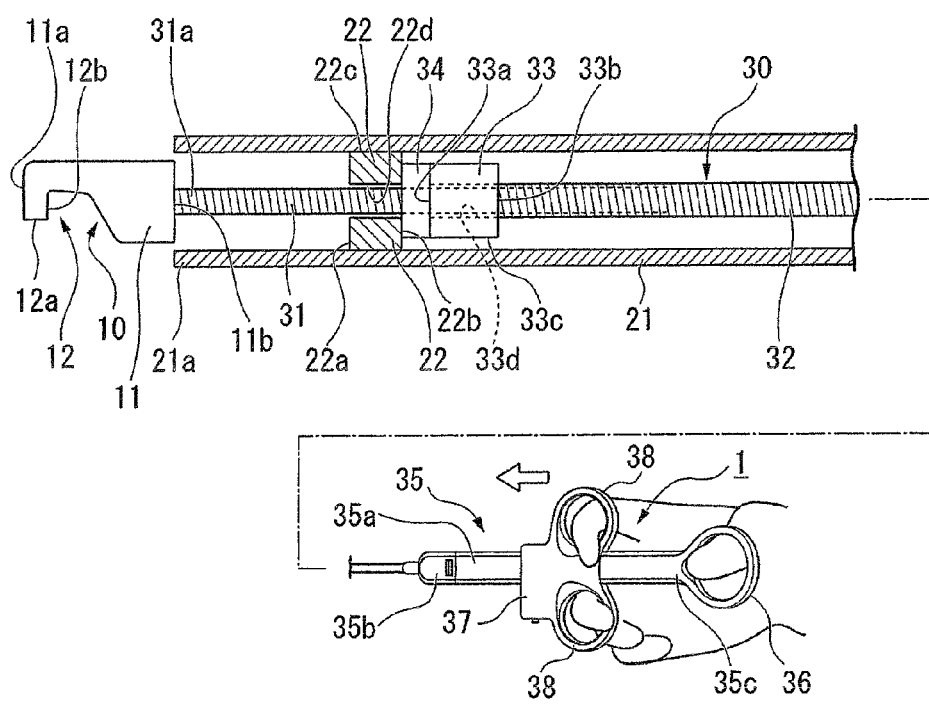
Figure 4:
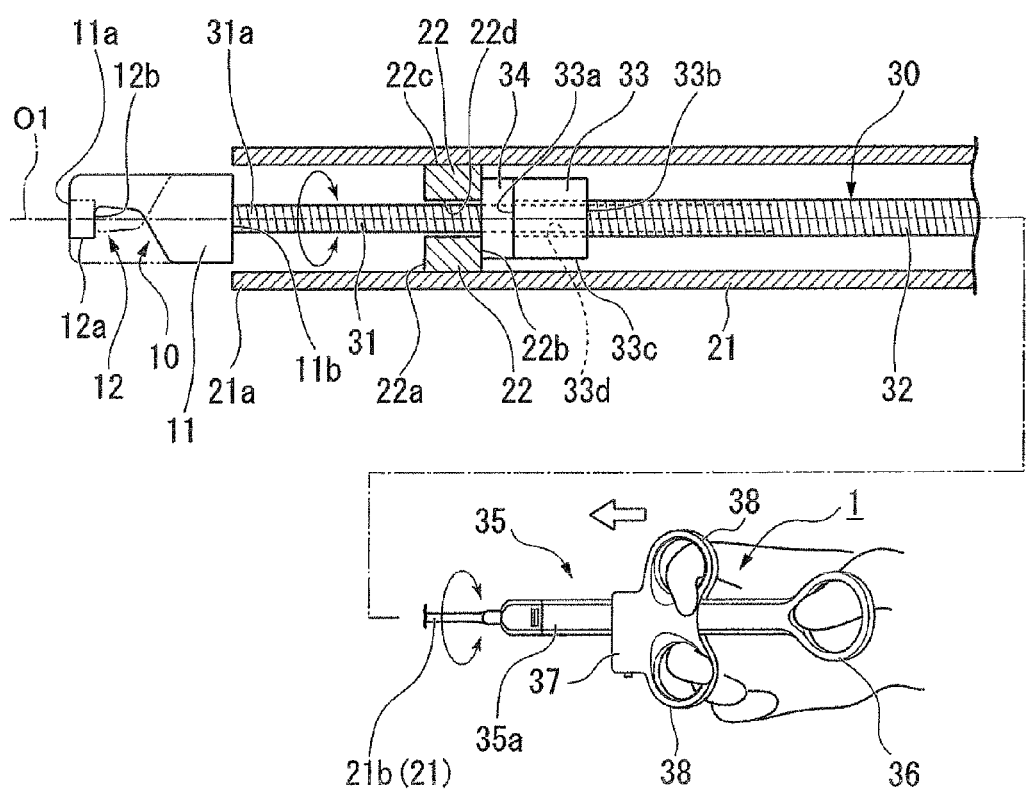
FIG. 4 is an illustrative view for describing the operation of the medical device.

FIGS. 3A to 4 are illustrative views for describing the operation of the medical device 1. FIG. 3A shows the positional relationship that respective portions of the medical device 1 when the medical device 1 is inserted into the treatment device channel of an endoscope to guide the treatment portion 10 to a treatment target site, and when the medical device 1 is pulled out of the treatment device channel of the endoscope after the completion of the treatment.

As shown in FIG. 3A, the operator holds the operation portion 35 with one hand by hooking their thumb in the finger-hooking portion 36 of the operation portion 35 and their index finger and middle finger into the respective finger-hooking portions 38. Also, the operator slides the sliding member 37 so as to move it with respect to the operation body 35a, thereby making the finger-hooking portion 36 close to the finger-hooking portions 38. As a result, the operation wire 31 and the inner tube 32 fixed to the sliding member 37 are pulled to the proximal end 35c side of the operation body 35a, and the treatment portion 10 fixed to the distal end 31a of the operation wire 31 is pulled into the outer tube 21.

When the operator slides the sliding member 37 to move it in the direction in which the finger-hooking portion 36 and the finger-hooking portions 38 become close to each other, the proximal end 11b of the incisional electrode body 11 contacts the distal end 22a of the regulation member 22. As a result, since the incisional electrode body 11 has a size which is enable to pass through the through-hole portion 22d of the regulation member 22, the incisional electrode body 11 is positioned at the position where it contacts the distal end 22a of the regulation member 22. At this time, the hook portion 12 provided at the distal end 11a side of the incisional electrode body 11 is accommodated in the outer tube 21.

The operator holds the outer tube 21 by the hand on the opposite side to the hand holding the operation portion 35 and inserts the outer tube 21 into the treatment device channel of the endoscope from the distal end 21a side of the outer tube 21. At this time, since the treatment portion 10 is accommodated in the outer tube 21, the hook tip portion 12a or the like of the hook portion 12 is not stuck in the inner wall surface of the treatment device channel. The operator protrudes the distal end 21a of the outer tube 21 from the distal end of the treatment device channel and guides the distal end 21a of the outer tube 21 to the treatment target site while viewing an image captured by using the endoscope.

FIG. 3B shows the positional relationship of respective portions when the treatment is performed on the treatment target site by using the treatment portion 10 of the medical device 1.

When the distal end 21a of the outer tube 21 is guided to the treatment target site, the operator slides the sliding member 37 to move it with respect to the operation body 35a in the direction in which the finger-hooking portion 36 and the finger-hooking portions 38 are separated from each other, as shown in FIG. 3B. As a result, the operation wire 31 and the inner tube 32 fixed to the sliding member 37 are pulled to a distal end 35b side of the operation body 35a, and the treatment portion 10 (incisional electrode body 11) fixed to the distal end 31a of the operation wire 31 is drawn outside the outer tube 21.

When the operator slides the sliding member 37 so as to move it with respect to the operation body 35a in the direction in which the finger-hooking portion 36 and the finger-hooking portions 38 are separated from each other, the distal end 33a of the contacting member 33 fixed to the inner tube 32 moves to the distal end 21a side of the outer tube 21. As a result, the rotating bearing member 34 is interposed between the contacting member 33 and the regulation member 22 as shown in FIG. 3B, so the contacting member 33 cannot move any farther toward the distal end 21a side of the outer tube 21. At this time, the incisional electrode body 11 of the treatment portion 10 is positioned outside the outer tube 21. In this positional relationship, it is possible to bring the hook portion 12 provided in the distal end 11a side of the incisional electrode body 11 into contact with body tissue or the like.

FIG. 4 is an operation-illustrating view for describing the operation of the hook portion 12 in the medical device 1.

As shown in FIG. 4, while the hook portion 12 is exposed outside the distal end 21a of the outer tube 21, the operator changes the direction of the hook tip portion 12a of the hook portion 12 to guide the hook portion 12 to the incision line determined by the operator in the treatment target site in some cases. At this time, while holding the operation portion 35, the operator holds the outer surface of the proximal end 21b of the outer tube 21 with a hand opposite to the hand holding the operation portion 35 and rotates the operation body 35a of the operation portion 35 around the axis of the outer tube 21.

The outer tube 21 and the operation body 35a are connected to each other so as to freely perform relative rotation. Accordingly, when the operator rotates the operation body 35a around the axis of the outer tube 21, the operation wire 31 and the inner tube 32 fixed to the sliding member 37 of the operation body 35a rotate around the axis of the outer tube 21 inside the outer tube 21. At this time, in order to maintain a drawn-out length by which the incisional electrode body 11 is drawn outside from the distal end 21a of the outer tube 21, the operator opens their hand to separate the finger-hooking portion 36 from the finger-hooking portions 38. Accordingly, at the distal end 21a side of the outer tube 21, the contacting member 33 fixed to the operation wire 31 and the inner tube 32 push the rotating bearing member 34 to the regulation member 22.

In the contacting member 33, the force causing the contacting member 33 and the regulation member 22 to perform the relative rotation around the central axis line (central axis line O1) of the operation wire 31 and the inner tube 32 and the force pushing the contacting member 33 to the rotating bearing member 34 act. Herein, the contacting member 33 and the rotating bearing member 34 freely perform the relative rotation around the axes of the operation wire 31 and the inner tube 32, and the rotating bearing member 34 and the regulation member 22 freely perform the relative rotation around the axes of the operation wire 31 and the inner tube 32. That is, in the medical device 1 of the present embodiment, there are two pairs of surfaces freely performing the relative rotation due to the rotating bearing member 34 provided between the contacting member 33 and the regulation member 22.

Accordingly, if at least one of between the contacting member 33 and the rotating bearing member 34 or between the rotating bearing member 34 and the regulation member 22 can perform relative rotation around the central axis line O1, the contacting member 33 and the regulation member 22 can perform the relative rotation. In the present embodiment, when the rotating bearing member 34 is formed of a material for which friction coefficients of the rotating bearing member 34 with the regulation member 22 and with the contacting member 33 are smaller than a friction coefficient between the regulation member 22 and the contacting member 33, it is possible to further increase the possibility that the contacting member 33 and the regulation member 22 can perform the relative rotation, compared to the case where the rotating bearing member 34 is not provided.

Even when the friction coefficient between the contacting member 33 and the rotating bearing member 34 and the friction coefficient between the rotating bearing member 34 and the regulation member 22 are the same as the friction coefficient between the contacting member 33 and the regulation member 22, it is also possible to further increase the possibility that the contacting member 33 and the regulation member 22 can perform the relative rotation, compared to the case where the rotating bearing member 34 is not provided.

Accordingly, it is possible for the operator to change the direction of the hook tip portion 12a of the hook portion 12 by rotating the operation body 35a with respect to the outer tube 21, while the incisional electrode body 11 of the treatment portion 10 is drawn out from the distal end 21a of the outer tube 21.

Furthermore, a plurality of rotating bearing members 34 may be provided. In this case, the hook portion 12 can further easily rotate with respect to the outer tube 21.

Hereinafter, an example of a procedure performed by using the medical device 1 will be described with reference to FIGS. 5A to 6B, by exemplifying a procedure in which the mucous membrane in a body cavity is removed endoscopically. FIGS. 5A to 6B are process-illustrating views for describing the process of the procedure performed by using the medical device 1.

Figure 5A:
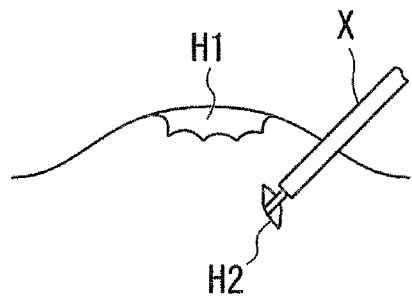
FIGS. 5A, 5B, 5C and 5D are illustrative views for describing a procedure performed by using the medical device.

First, through an endoscope (not shown), an injection needle (also not shown) is introduced into a body cavity. Thereafter, as shown in FIG. 5A, physiological saline is injected into submucosa of a lesioned mucous membrane portion H1 as the treatment target site that is to be excised from the body cavity to raise the lesioned mucous membrane portion H1, thereby performing the initial incision for making a hole H2 in a portion of the mucous membrane of the periphery of the lesioned mucous membrane portion H1. In order to perform the initial incision, a proper high frequency incisional device X which includes a needle-like electrode and incises the body tissue when high frequency current pass therethrough can be introduced through an endoscope for use.

Figure 5B:
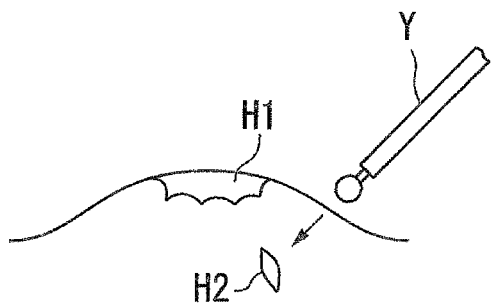
Figure 5C:
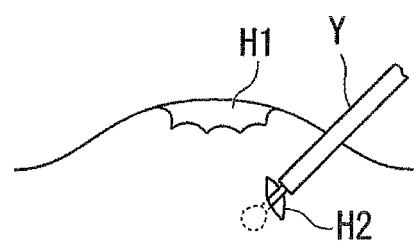
Figure 5D:
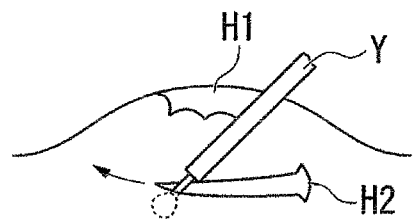

Subsequently, as shown in FIG. 5B, a proper high frequency incisonal device Y which includes a needle-like electrode having a spherical insulator at its distal end is guided to the lesioned mucous membrane portion H1 through the endoscope, and the needle-like electrode of the high frequency incisional device Y is inserted into the hole H2 as shown in FIG. 5C. Further, while the high frequency current is supplied to the needle-like electrode of the high frequency incisional device Y, the needle-like electrode is moved to incise the mucosal layer of the periphery of the lesioned mucous membrane portion H1, as shown in FIG. 5D.

Figure 6A:
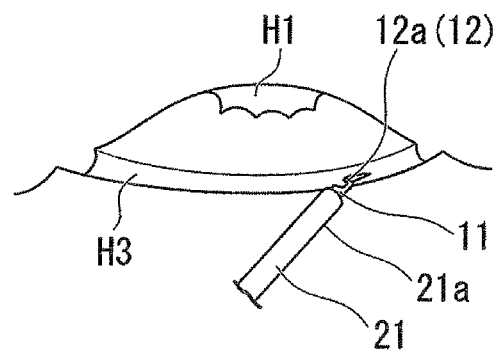
FIGS. 6A and 6B are illustrative views for describing a procedure performed by using the medical device.

As shown in FIG. 6A, after the incision is made all around the mucosal layer such that the incision surrounds the lesioned mucous membrane portion H1, the operator guides the medical device 1 to the lesioned mucous membrane portion H1 through the endoscope. The medical device 1 is held in the initial state where the incisional electrode body 11 is pulled into the outer tube 21 in advance. In this state, the operator introduces the medical device 1 into the body cavity through the treatment device channel of the endoscope. Also, the operator brings the incisional electrode body 11 into contact with an incision opening H3 created by incising the periphery of the lesioned mucous membrane portion H1 and hooks the hook tip portion 12a of the hook portion 12 to the incision opening H3, thereby incising and dissecting the sublayer of the lesioned mucous membrane portion H1. At this time, it is preferable that the hook tip portion 12a of the hook portion 12 is parallel to the muscularis propria or faces the lumen side.

Figure 6B:
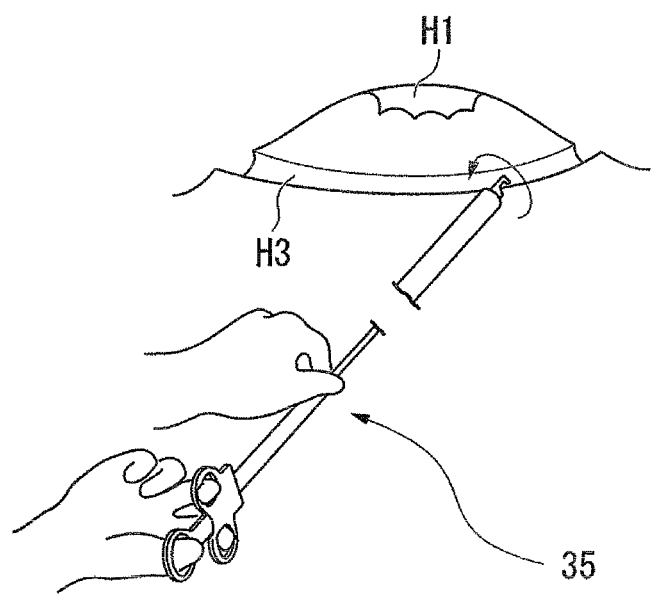

In addition, when the hook tip portion 12a does not face the preferable direction as described above, as in the description made with reference to FIG. 4, the direction of the hook tip portion 12a of the hook portion 12 is adjusted, thereby adjusting the direction of the hook tip portion 12a as shown in FIG. 6B. At this time, in the medical device 1 of the present embodiment, it is not necessary to slide the sliding member 37 to move it with respect to the operation body 35a, and the drawn-out amount in which the incisional electrode body 11 is drawn out from the distal end 21a of the outer tube 21 does not change.

After the entire lesioned mucous membrane portion H1 is dissected, the lesioned mucous membrane portion H1 is taken out of the body through the endoscope while being held with grasping forceps (not shown) or the like, thereby completing a series of procedures.

Conventionally, in a state where the hook tip portion is pushed out to the distal end side of the outer tube, the treatment portion and the outer tube are under frictional engagement. Therefore, in this state, it is difficult for the treatment portion to rotate around the axis of the outer tube in some cases even when an operation for rotating the treatment portion is performed in the operation portion.

In contrast, according to the medical device 1 of the present embodiment, since the rotating bearing member 34 is provided between the contacting member 33 and the regulation member 22, the contacting member 33 and the rotating bearing member 34 can relatively rotate around the axis, and the rotating bearing member 34 and the regulation member 22 can relatively rotate around the axis. Accordingly, even when torque is applied to the operation portion while the contacting member 33 is pushed to the regulation member 22 side, it is easy to rotate the treatment portion 10 with respect to the outer tube 21.

Moreover, since the rotating bearing member 34 is formed of a material for which the friction coefficient between the contacting member 33 and the rotating bearing member 34 and the friction coefficient between the rotating bearing member 34 and the regulation member 22 are smaller than the friction coefficient between the regulation member 22 and the contacting member 33, even when the torque is applied to the operation portion while the contacting member 33 is pushed to the regulation member 22 side, it is made further easier to rotate the treatment portion 10 with respect to the outer tube 21.

Second Embodiment

Next, a medical device 2 of a second embodiment of the present invention will be described with reference to FIGS. 7A to 8.

Figure 7A:
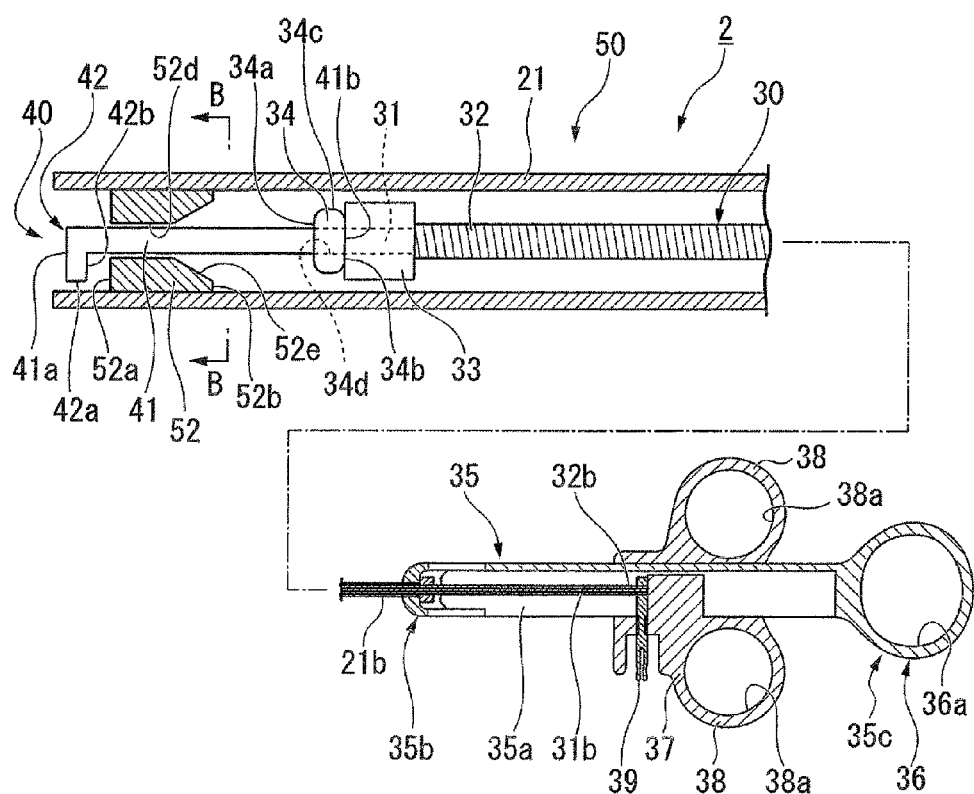
FIG. 7A is a partial cross sectional view showing a medical device of a second embodiment of the present invention.
Figure 7B:
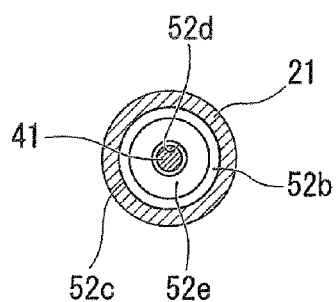
FIG. 7B is a cross sectional view taken along a line B-B of FIG. 7A.

FIG. 7A is a cross sectional view showing a part of the configuration of the medical device 2, and FIG. 7B is a cross sectional view taken along a line B-B of FIG. 7A. Also, in each embodiment described below, portions common to the configuration of the medical device 1 of the first embodiment are marked by the same reference numerals, and the description thereof will not be repeated.

As shown in FIGS. 7A and 7B, the configuration of the medical device 2 differs from that of the medical device 1 described in the first embodiment in that the medical device 2 includes a treatment portion 40 provided instead of the treatment portion 10 and the insertion portion 50 provided instead of the insertion portion 20.

The treatment portion 40 is a hook type treatment portion that looks like a hook formed of a wire rod (incisional electrode body) 41 bent at a distal end 41a side. In the embodiment, the wire rod 41 is fixed to the operation wire 31 in the contacting member 33 by welding, for example. Further, the wire rod 41 and the operation wire 31 may be integrally formed with the same material.

The wire rod 41 is inserted in the through-hole portion 34d of the rotating bearing member 34. In the embodiment, the shape of the outer surfaces between the distal end 34a and an outer circumferential surface 34c and between the outer circumferential surface 34c and the proximal end 34b in the rotating bearing member 34 are formed into a substantially round shape.

The insertion portion 50 includes the outer tube 21 described in the first embodiment and the regulation member 52 provided at the distal end 21a side of the outer tube 21 instead of the regulation member 22.

In the regulation member 52, a tapered surface 52e having the internal diameter gradually increasing from a distal end 52a toward a proximal end 52b is formed in the proximal end 52b side in a through-hole portion 52d.

The tapered surface 52e is obliquely formed so that the internal diameter of the distal end 52a side is smaller than the external diameter of the rotating bearing member 34 and so that the internal diameter of the proximal end 52b is the same as or larger than the external diameter of the rotating bearing member 34.

Further, as the material for the regulation member 52, it is possible to use a resin material, a metal or the like just like the regulation member 22 described in the first embodiment.

Figure 8:
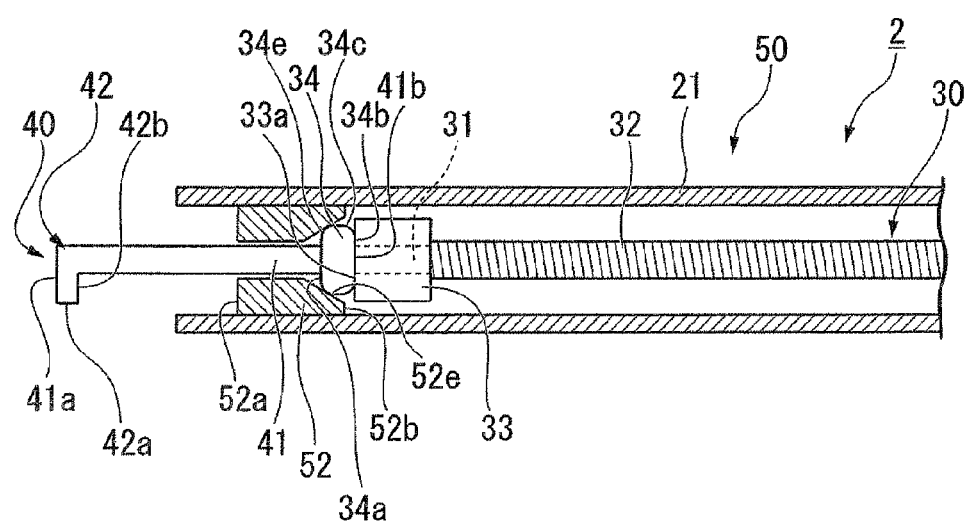
FIG. 8 is an operation-illustrating view for describing the operation of the medical device at the time of use.

FIG. 8 is an operation-illustrating view for describing the operation of the medical device 2 at the time of use and shows positional relationships of respective portions when the treatment portion 40 is drawn out from the distal end 21a of the outer tube 21. As shown in FIG. 8, when the treatment portion 40 is drawn outside from the distal end 21a of the outer tube 21, a chamfered angle 34e between the distal end 34a and the outer circumferential surface 34c of the rotating bearing member 34 is brought into line contact with the tapered surface 52e circularly. In addition, at this time, the proximal end 34b of the rotating bearing member 34 is brought into surface contact with the distal end 33a of the contacting member 33.

In the embodiment, the contact area between the rotating bearing member 34 and the regulation member 52 is smaller than the contact area between the rotating bearing member 34 and the contacting member 33. Therefore, the contacting member 33 and the regulation member 52 more easily perform the relative rotation around the axis compared to the combination of the contacting member 33 and the regulation member 22 in the medical device 1 described in the first embodiment. As a result, according to the medical device 2 of the present embodiment, even when torque is applied to the operation portion while the contacting member 33 is pushed to the regulation member 22, it is easy to rotate the treatment portion 40 with respect to the outer tube 21.

Third Embodiment

Next, a medical device 3 of a third embodiment of the present invention will be described with reference to FIGS. 9A, 9B and 9C.

Figure 9A:
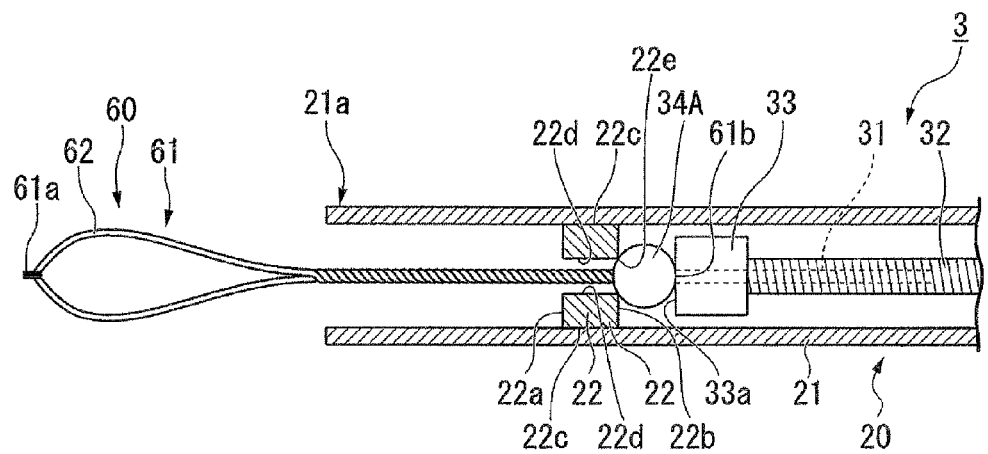
FIG. 9A is a partial cross sectional view showing a part of the configuration of a medical device of a third embodiment of the present invention.

FIG. 9A is a cross sectional view showing a part of the configuration of the medical device 3. Also, FIG. 9B is a cross sectional view showing a rotating bearing member 34A in the medical device 3, and FIG. 9C is a front view taken when the rotating bearing member 34A is viewed from a distal end 34Aa side toward a proximal end 34Ab side.

Figure 9B:
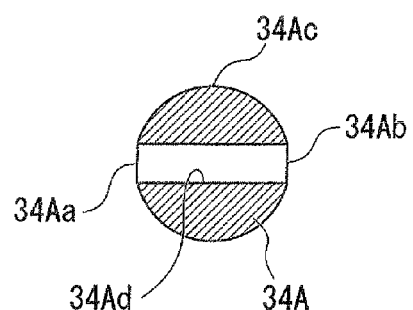
FIG. 9B is a cross sectional view showing a rotating bearing member in the medical device.
Figure 9C:
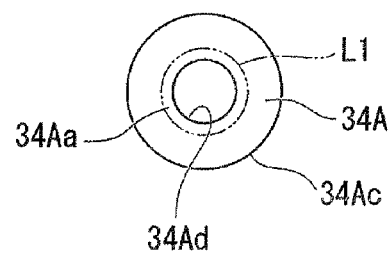
FIG. 9C is a front view showing the rotating bearing member.

As shown in FIGS. 9A, 9B and 9C, the configuration of the medical device 3 differs from that of the medical device 1 of the first embodiment in that the medical device 3 includes a treatment portion 60 provided instead of the treatment portion 10 and the rotating bearing member 34A provided instead of the rotating bearing member 34.

The treatment portion 60 is a snare type treatment portion having a length of wire rod (incisional electrode body) 61 bound in a proximal end 61b.

The wire rod 61 is bent at a distal end 61a, and a loop portion 62 which becomes a ring shape in a natural state is formed at a side advancing toward the proximal end 61b from the distal end 61a. The wire rod 61 is inserted in the through-hole portion 22d of the regulation member 22. In addition, though not shown in the drawing, the regulation member 22 may include a stopper or the like which is provided across the inside of the loop portion 62 to prevent the wire rod 61 from coming off to the proximal end 22b side through the inside of the through-hole portion 22d.

The rotating bearing member 34A is formed into a spherical shape; also, in the rotating bearing member 34A, there is formed a through-hole portion 34Ad having a central axis line penetrating through the center of the sphere. The external diameter of the rotating bearing member 34A is larger than the internal diameter of the through-hole portion 22d and smaller than the internal diameter of the outer tube 21.

As shown in FIGS. 9A and 9C, the rotating bearing member 34A is brought into line contact with an angle portion 22e of the proximal end 22b side in the through-hole portion 22d of the regulation member 22 circularly. A circular line L1 shown in FIG. 9C shows a position where the angle portion 22e between the through-hole portion 22d and the proximal end 22b of the regulation member 22 contacts. Furthermore, a proximal end 34Ab of the rotating bearing member 34A is brought into line contact with the distal end 33a of the contacting member 33.

In the present embodiment, the contacting member 33 is brought into line contact with the rotating bearing member 34A, and the rotating bearing member 34A is brought into line contact with the regulation member 22. Accordingly, the contacting member 33 and the regulation member 22 more easily perform the relative rotation around the axis, compared to a combination of the contacting member 33 and the regulation member 22 through the rotating bearing member 34 in the medical device 1 described in the first embodiment. As a result, according to the medical device 3 of the present embodiment, even when torque is applied to the operation portion while the contacting member 33 is pushed to the regulation member 22, it is easy to rotate the treatment portion 60 with respect to the outer tube 21.

Fourth Embodiment

Next, a medical device 4 of a fourth embodiment of the present invention will be described with reference to FIGS. 10A and 10B.

Figure 10A:
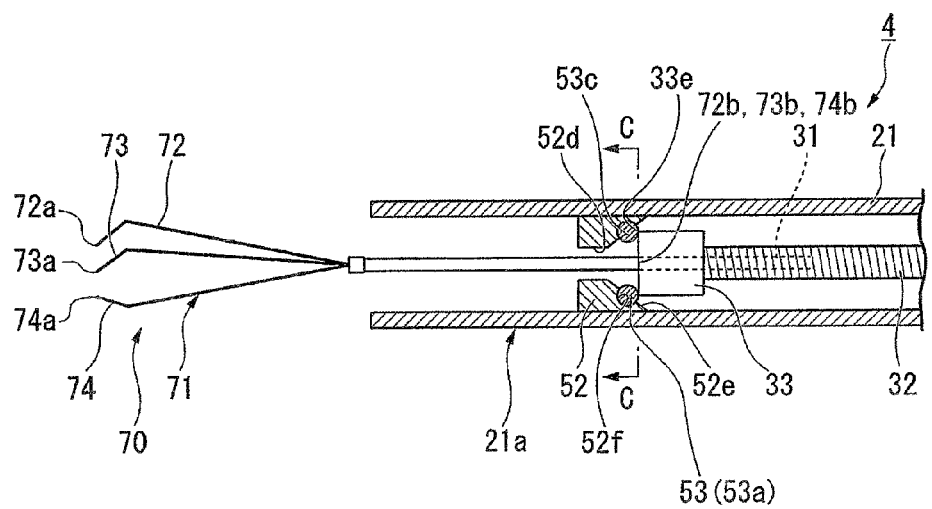
FIG. 10A is a partial cross sectional view showing a part of the configuration of a medical device of a fourth embodiment of the present invention.
Figure 10B:
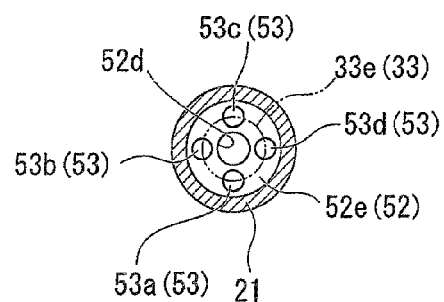
FIG. 10B is a cross sectional view taken along a line C-C of FIG. 10A.

FIG. 10A is a cross sectional view showing a part of the configuration of the medical device 4, and FIG. 10B is a cross sectional view taken along a line C-C of FIG. 10A.

As shown in FIGS. 10A and 10B, the configuration of the medical device 4 differs from that of the medical device in each embodiment described above in that the medical device 4 is provided with a treatment portion 70 instead of the treatment portion 10, and that the rotating bearing member 53 provided instead of the rotating bearing member 34 is attached on the regulation member 52 fixed to the outer tube 21.

The treatment portion 70 is a tripod type treatment portion having a tripod portion 71 including a wire rod (a first electrode) 72, a wire rod (a second electrode) 73, and a wire rod (a third electrode) 74.

All of the wire rods 72, 73, and 74 are formed of a material having electric conductivity and elasticity. Specifically, as the material for the wire rods 72, 73, and 74, it is possible to use stainless steel. The wire rods 72, 73, and 74 are bound together at proximal ends 72b, 73b, and 74b and are fixed by welding or brazing, or the like, for example.

Further, the wire rods 72, 73, and 74 respectively extend in a direction in which they are separated from each other as they proceed toward distal ends 72a, 73a, and 74a from the proximal ends 72b, 73b, and 74b. Furthermore, the wire rods 72, 73, and 74 bend in a direction in which they get close to each other at the distal ends 72a, 73a, and 74a.

The treatment portion 70 is so configured such that the body tissue can be incisized with the cauterization by bringing the wire rods 72, 73, and 74 of the tripod portion 71 into contact with the body tissue and applying the high frequency current to the wire rods 72, 73, and 74.

In the regulation member 52, a substantially hemispherical shape of concave portion 52f is formed at the tapered surface 52e. Each concave portion 52f is provided with a spherical shape of a rotating bearing member 53 (including rotating bearing members 53a, 53b, 53c and 53d). The rotating bearing member 53 is fitted in the concave portion 52f and supported by the concave portion 52f. Also, the rotating bearing member 53 freely rotates around its own center. As shown in FIG. 10B, when the regulation member 52 is viewed from the proximal end 52b side toward the distal end 52a side, a plurality of rotating bearing members 53 is provided while being separated in the circumferential direction. It is preferable that three of the rotating bearing members 53 are provided at positions separate from each other, since one plane can be defined with this configuration. It is also preferable that three or more of the rotating bearing members 53 are provided. In the present embodiment, four rotating bearing members 53 are provided.

As shown in FIGS. 10A and 10B, in the present embodiment, when the treatment portion 70 is drawn out from the distal end 21a of the outer tube 21, the angle portion 33e between the distal end 33a and the outer circumferential surface 33c of the contacting member 33 contacts each outer surface of the rotating bearing member 53. At this time, the angle portion 33e of the contacting member 33 is brought into point contact with the outer surface of the rotating bearing member 53. In addition, when the treatment portion 70 and the outer tube 21 perform the relative rotation while the angle portion 33e of the contacting member 33 is brought into contact with the outer surface of the rotating bearing member 53, the rotating bearing member 53 rolls. Accordingly, between the angle portion 33e of the contacting member 33 and the outer surface of the rotating bearing member 53, rolling friction smaller than sliding friction occurs.

In this manner, in the present embodiment, the contacting member 33 is brought into contact with the rotating bearing member 53 in a state of point contact, and the friction occurring between the contacting member 33 and the rotating bearing member 53 is rolling friction. Therefore, the contacting member 33 and the regulation member 52 more easily perform the relative rotation around the axis, compared to a combination of the contacting member 33 and the regulation member 22 through the rotating bearing member 34 in the medical device 1 described in the first embodiment. As a result, according to the medical device 4 of the present embodiment, even when torque is applied to the operation portion while the contacting member 33 is pushed to the regulation member 52 side, it is easy to rotate the treatment portion 70 with respect to the outer tube 21.

Fifth Embodiment

Next, a medical device 5 of a fifth embodiment of the present invention will be described with reference to FIGS. 11A to 12.

Figure 11A:
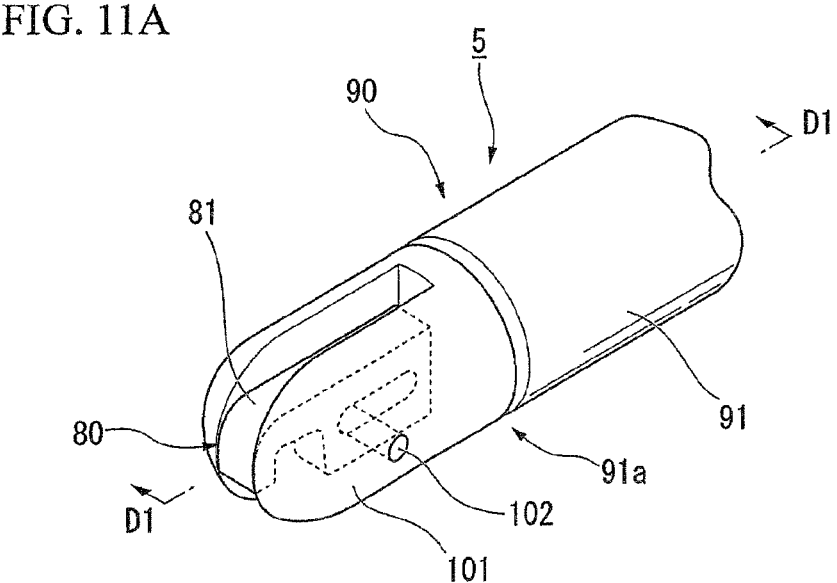
FIG. 11A is a perspective view showing a part of the configuration of a medical device of a fifth embodiment of the present invention.

FIG. 11A is a perspective view showing a part of the configuration of the medical device 5. As shown in FIG. 11A, the configuration of the medical device 5 of the embodiment differs from that of the medical device 1 of the first embodiment in that it includes a treatment portion 80 provided instead of the treatment portion 10, an insertion portion 90 provided instead of the insertion portion 20 and a transmission portion 100 provided instead of the transmission portion 30.

Figure 11B:
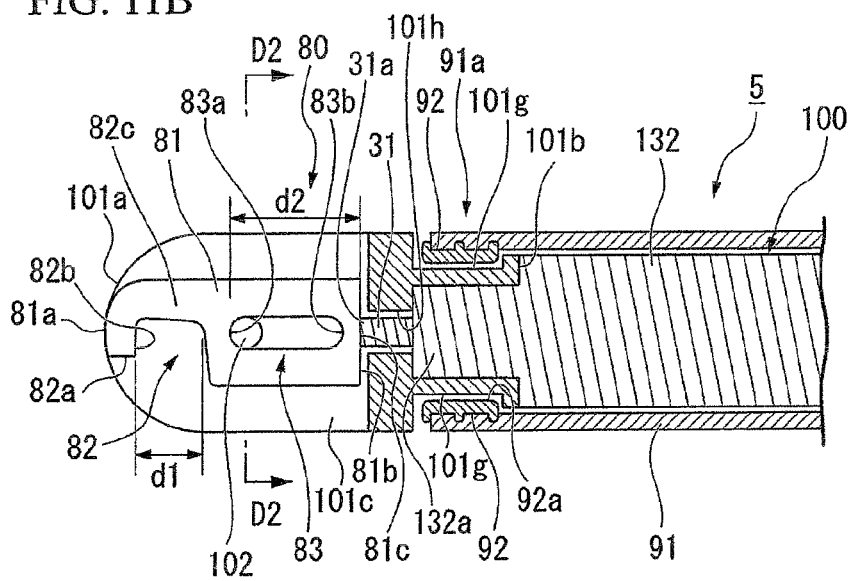
FIG. 11B is a partial cross sectional view taken along a line D1-D1 of FIG. 11A.

FIG. 11B is a partial cross sectional view showing the configuration of the vicinity of the treatment portion 80 in the medical device 5 and being taken along a line D1-D1 of FIG. 11A. As shown in FIGS. 11A and 11B, the treatment portion 80 is a hook type treatment portion for incising the body tissue with the cauterization while contacting the body tissue. The treatment portion 80 includes an incisional electrode body 81 having electric conductivity. In the incisional electrode body 81, there is formed a hook-like hook portion 82 at a distal end 81a side. Furthermore, the distal end 31a of the same operation wire 31 as in the first embodiment is fixed to a proximal end 81b side of the incisional electrode body 81.

The shape of the incisional electrode body 81 is a substantially plate-like shape, and in a position close to the proximal end 81b from the hook portion 82, there is formed a slit portion 83 extending in a direction facing a fixing portion 81c from the hook portion 82.

Figure 11C:
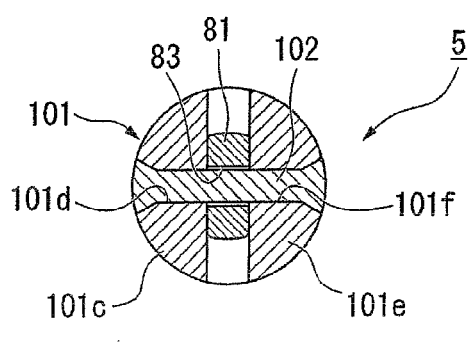
FIG. 11C is a partial cross sectional view taken along a line D2-D2 of FIG. 11B.

FIG. 11C is a cross sectional view taken along a line D2-D2 of FIG. 11B. As shown in FIGS. 11B and 11C, the slit portion 83 is formed while penetrating the incisional electrode body 81 in its thickness direction and is formed into an elongated hole shape in which a maximum value (a major axis d2) of the length obtained when the slit portion 83 extends in a surface direction of the incisional electrode body 81 is longer than that of a length d1 of an axis portion 82c formed with a narrow width in the incisional electrode body 81.

The hook portion 82 provided at the distal end 81a side of the incisional electrode body 81 is formed into the same shape as the hook portion 12 described in the first embodiment.

The insertion portion 90 includes an outer tube 91 provided instead of the outer tube 21 described in the first embodiment and a bearing 92 interlockingly fixed to the inner circumferential surface of a distal end 91a of the outer tube 91.

It is preferable that the outer tube 91 is formed of a material having an insulation property just like the outer tube 21. Further, unlike the outer tube 21, the outer tube 91 positions the treatment portion 80 so that the treatment portion 80 is positioned outside the outer tube 91.

The bearing 92 is formed into a ring shape, and the outer circumferential surface of the bearing 92 is fixed to the inner circumferential surface of the outer tube 91 by adhesion, or the like, for example. As a material for the bearing 92, a resin material or the like having an insulation property can be used; also, it is possible to use the same material as the rotating bearing member 34 described in the first embodiment. Furthermore, it is preferable that the bearing 92 is formed of a material which exhibits a small friction coefficient with a hook accommodating portion 101 described later.

The transmission portion 100 includes an inner tube 132 instead of the inner tube 32, a hook accommodating portion 101 fixed to a distal end 132*a* of the inner tube 132 and a regulation member 102 fixed to the hook accommodating portion 101.

The operation wire 31 is inserted in the inner tube 132 so that the operation wire 31 freely advances or retreats. Also, in the distal end 35*b* of the operation body 35*a* shown in FIG. 12, the inner tube 132 is fixed not to the contact electrode portion 39 but to the operation body 35*a*. That is, in the present embodiment, since the inner tube 132 is fixed to the operation body 35*a*, the inner tube 132 performs advancing or retreating movement relatively with respect to the sliding member 37.

As shown in FIG. 11C, the hook accommodating portion 101 includes a first wall portion 101*c* and a second wall portion 101*e* which are provided while being separated from each other in the thickness direction of the incisional electrode body 81 and interposing the incisional electrode body 81 therebetween. In the first wall portion 101*c* and the second wall portion 101*e* respectively, surfaces facing the incisional electrode body 81 are formed to be parallel to each other. The gap between the first wall portion 101*c* and the second wall portion 101*e* is set to a distance obtained by combining the thickness of the incisional electrode body 81 and the minute clearance. Between the first wall portion 101*c* and the second wall portion 101*e*, the incisional electrode body 81 can move relatively with respect to the hook accommodating portion 101.

In the present embodiment, the first wall portion 101*c* and the second wall portion 101*e* are integrally formed by being linked to each other at their proximal end portions respectively.

As shown in FIG. 11C, in the first wall portion 101*c*, there is provided a through-hole portion 101*d* formed while penetrating the first wall portion 101*c* in the thickness direction of the incisional electrode body 81. Also, in the second wall portion 101*e*, there is provided a through-hole portion 101*f* formed while penetrating the second wall portion 101*e* coaxially with the through-hole portion 101*d* in the thickness direction of the incisional electrode body 81. The through-hole portions 101*d* and 101*f* are so formed such that the opening size of opening end portions facing in opposite directions to each other is larger than the opening size of opening end portions facing each other.

As shown in FIG. 11C, the regulation member 102 inserted in the through-hole portion 101*d* and the through-hole portion 101*f* is formed into a substantially cylindrical shape in which both ends in the axial direction are more widened toward the outside of the radial direction than in the middle portion. This configuration is formed by deforming both ends of the regulation member 102 after the regulation member 102 is inserted into the through-hole portion 101*d* and the through-hole portion 101*f*, and the regulation member 102 is so configured that it does not come off the through-hole portion 101*d* and the through-hole portion 101*f*.

The size of the external diameter of the middle portion of the regulation member 102 is set such that the regulation member 102 can be inserted into the slit portion 83 formed in the incisional electrode body 81.

Further in a proximal end 101*b* side of the hook accommodating portion 101, there is formed an engagement concave portion 101*g* in which the bearing 92 is fitted. The bottom surface of the engagement concave portion 101*g* is so formed such that it slides with respect to the inner circumferential surface 92*a* of the bearing 92.

Further as shown in FIG. 11B, in the hook accommodating portion 101, there is provided a through-hole portion 101*h* which is so formed such that the direction of central axis line thereof is orthogonal to the central axis line of the regulation member 102. The operation wire 31 is inserted in the through-hole portion 101*h* so that the operation wire 31 freely advances or retreats.

The operation at the time of use of the medical device 5 with the above-described configuration of the present embodiment will be described with reference to FIG. 12. FIG. 12 is an illustrative view for describing the operation of the medical device 5 at the time of use.

In the medical device 5, the sliding member 37 performs an advancing or retreating operation with respect to the operation body 35*a* in the same manner as described in the first embodiment. As a result, the operation wire 31 fixed to the contact electrode portion 39 which is fixed to the sliding member 37 moves along the inner tube 132 in the inner portion of the inner tube 132.

Figure 12:
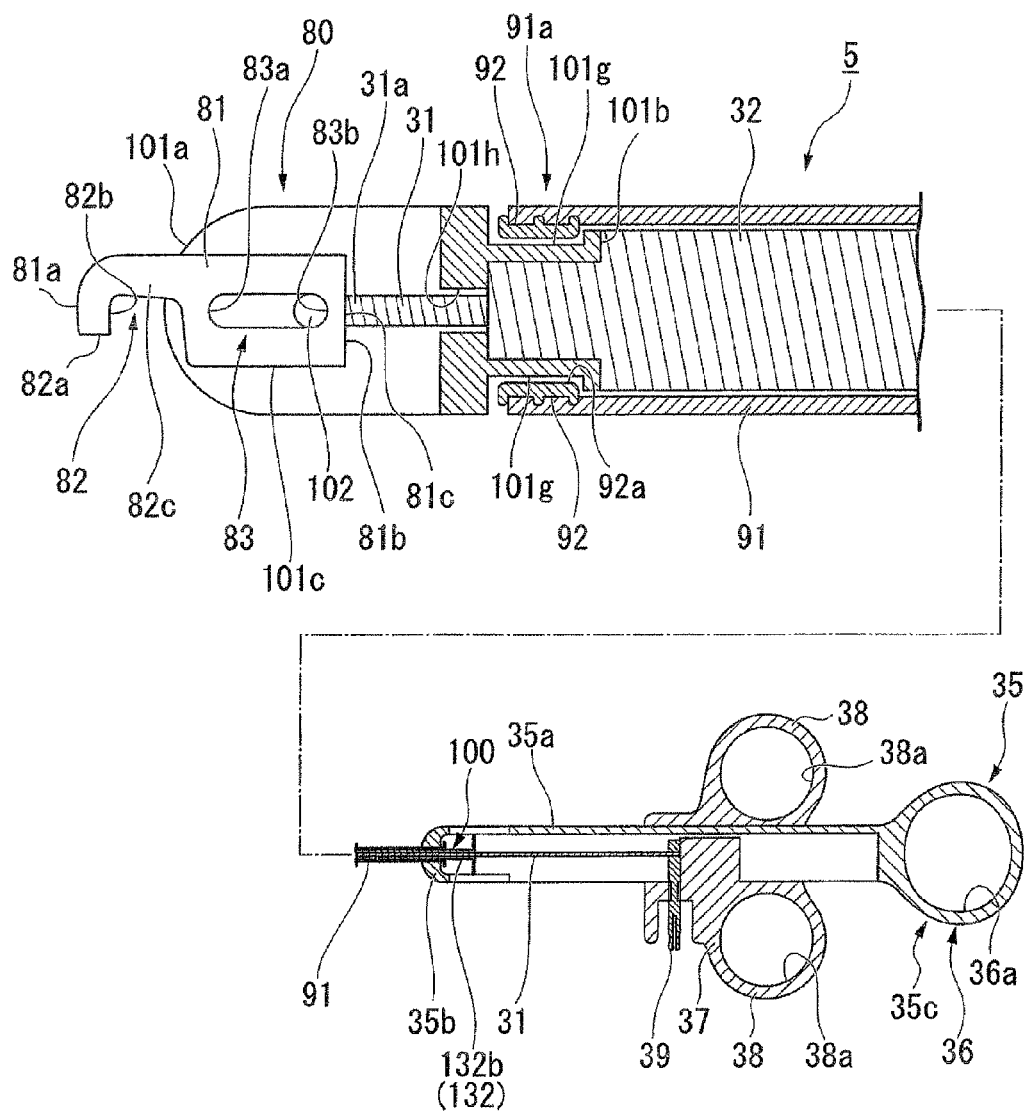
FIG. 12 is an operation-illustrating view for describing the operation of the medical device at the time of use.

As shown in FIG. 12, at the distal end 91*a* side of the outer tube 91, when the operation wire 31 is pushed out to the distal end 31*a* side, the distal end 31*a* of the operation wire 31 presses a fixing portion 81*c* of the incisional electrode body 81 to the distal end 81*a* side. As a result, while being supported by the first wall portion 101*c*, the second wall portion 101*e* (refer to FIG. 11C) and the regulation member 102, the incisional electrode body 81 moves in the direction of the distal end 81*a* under the guidance of the slit portion 83. Accordingly, the hook portion 82 provided at the distal end 81*a* side of the incisional electrode body 81 is drawn outside from the hook accommodating portion 101.

When the regulation member 102 contacts a proximal end 83*b* of the slit portion 83, the incisional electrode body 81 cannot move any further to the distal end 81*a* side. Since the major axis d2 of the slit portion 83 is larger than the length dl of the axis portion 82*c* in the hook portion 82, the hook portion 82 is exposed outside the hook accommodating portion 101.

In the present embodiment, the proximal end 83*b* in the slit portion 83 functions as the contacting member 33 fixed to the operation wire 31 through the inner tube 32 in each embodiment described above.

When the wall portion of the proximal end 83*b* side in the slit portion 83 contacs the regulation member 102, at least a hook tip portion 82*a* and an inner surface portion 82*b* of the hook portion 82 are drawn outside the hook accommodating portion 101.

Moreover, when the direction of the hook tip portion 82*a* of the hook portion 82 is adjusted in the same manner as described in the first embodiment, the operation body 35*a* shown in FIG. 1B is rotated around the axis of the outer tube 91 with respect to the outer tube 91 shown in FIG. 12. As a result, the inner tube 132 fixed to the operation body 35*a* rotates around the axis together with the operation body 35*a*, and the hook accommodating portion 101 fixed to the distal end 132*a* of the inner tube 132 performs the relative rotation around the axis integratedly with the inner tube 132. At this time, since the bearing 92 is provided between the hook accommodating portion 101 and the outer tube 91, the hook accommodating portion 101 and the outer tube 91 perform the relative rotation around the axis.

When the hook accommodating portion 101 is rotated by the relative rotation of the operation body 35*a* around the axis of the outer tube 91, the first wall portion 101*c* and the second wall portion 101e of the hook accommodating portion 101 integratedly rotate around the axis. As a result, the incisional electrode body 81 interposed between the first wall portion 101c and the second wall portion 101e also rotates around the axis. Accordingly, it is possible to adjust the direction of the hook tip portion 82a of the hook portion 82 to a desirable direction.

As described above, according to the medical device 5 of the present embodiment, the protruding length by which the hook portion 82 protrudes from the hook accommodating portion 101 due to the regulation member 102 and the slit portion 83 is regulated; furthermore, it is possible to make the outer tube 91 and the hook portion 82 perform the relative rotation around the axis by using the bearing 92 and the engagement concave portion 101g provided in the outer tube 91.

Further both the inner tube 132 and the outer tube 91 are connected to the operation body 35a. Accordingly, when the sliding member 37 slides to move with respect to the operation body 35a to draw the hook portion 82 outside the hook accommodating portion 101, the outer tube 91 and the inner tube 132 do not perform the relative rotation in the axial direction. As a result, the outer tube 91 and the inner tube 132 perform the relative rotation around the axis with light force. Accordingly, it is possible to adjust the direction of the hook tip portion 82a of the hook portion 82 while the hook portion 82 is drawn outside the hook accommodating portion 101.

Modified Example 1

Figure 13:
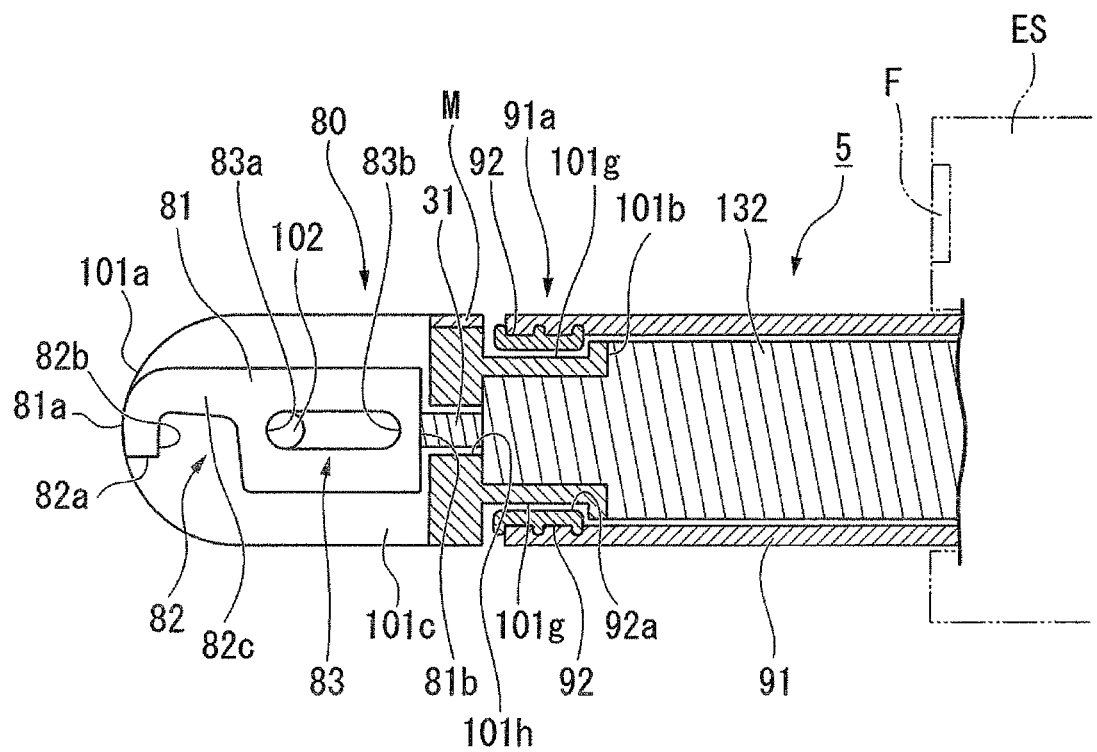
FIG. 13 is a partial cross sectional view showing the configuration of a modified example 1 of the medical device.

Hereinafter, the configuration in a modified example 1 of the medical device 5 of the present embodiment will be described with reference to FIG. 13. FIG. 13 is a cross sectional view showing a part of the configuration of the medical device 5 of the modified example.

As shown in FIG. 13, in the modified example, there is provided a marking portion M in a portion of the outer surface of the hook accommodating portion 101. The marking portion M is a portion for showing the direction of the hook tip portion 82a in the accommodating portion 101 to the operator who has seen the hook accommodating portion 101 by using the endoscope. As the marking portion M, it is possible to use one in which paint is filled in a concave portion created by digging out a portion of the outer surface of the hook accommodating portion 101, for example. Further, when the hook accommodating portion 101 is formed of a resin, it is possible to use one which is formed by scorching a portion of the outer surface of the hook accommodating portion 101 by using a laser and performing laser printing or the like for forming a pattern thereon, as the marking portion M.

It is preferable that the position in which the marking portion M is formed is provided between the first wall portion 101c and the second wall portion 101e. As shown in FIG. 13B, the position is preferably at a portion exposed outside the outer tube 91 at the proximal end side of the first wall portion 101c and the second wall portion 101e in the outer surface of the hook accommodating portion 101, so that the marking portion M comes into the visual field of an imaging portion F in an endoscope ES.

The marking portion M shows which direction the hook tip portion 82a of the hook portion 82 accommodated in the hook accommodating portion 101 faces, between the first wall portion 101c and the second wall portion 101e of the hook accommodating portion 101.

In the modified example, the marking portion M is provided in the hook accommodating portion 101. Therefore, even when the hook tip portion 82a is not drawn out from the hook accommodating portion 101, the operator can determine the direction of the hook tip portion 82a by determining whether the marking portion M is seen in the visual field of the imaging portion F.

Modified Example 2

Figure 14A:
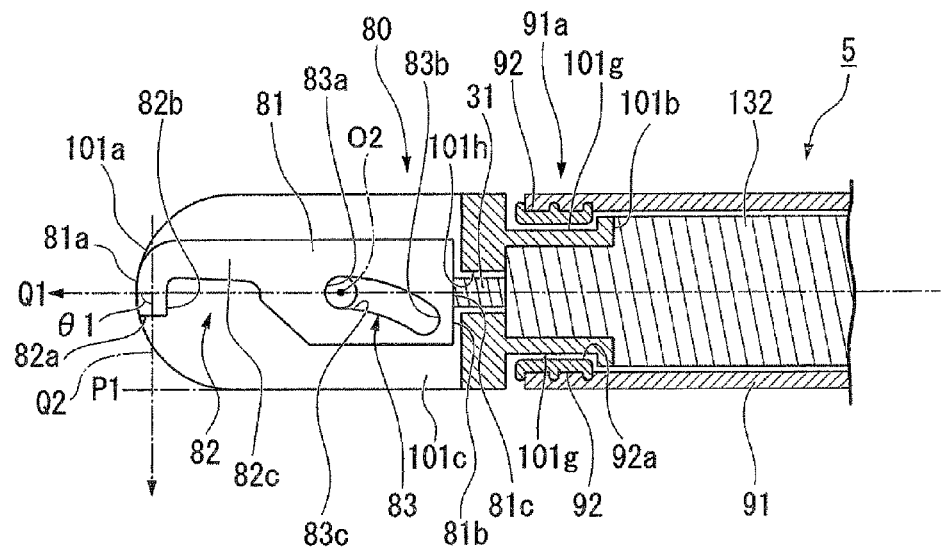
FIG. 14A is a partial cross sectional view showing the configuration of a modified example 2 of the medical device.

Hereinafter, the configuration in modified example 2 of the medical device 5 of the present invention will be described with reference to FIGS. 14A and 14B. FIG. 14A is a cross sectional view showing a part of the configuration of the medical device 5 of the modified example, and FIG. 14B is an operation-illustrating view for describing the operation of the medical device 5 of the modified example at the time of use.

Figure 14B:
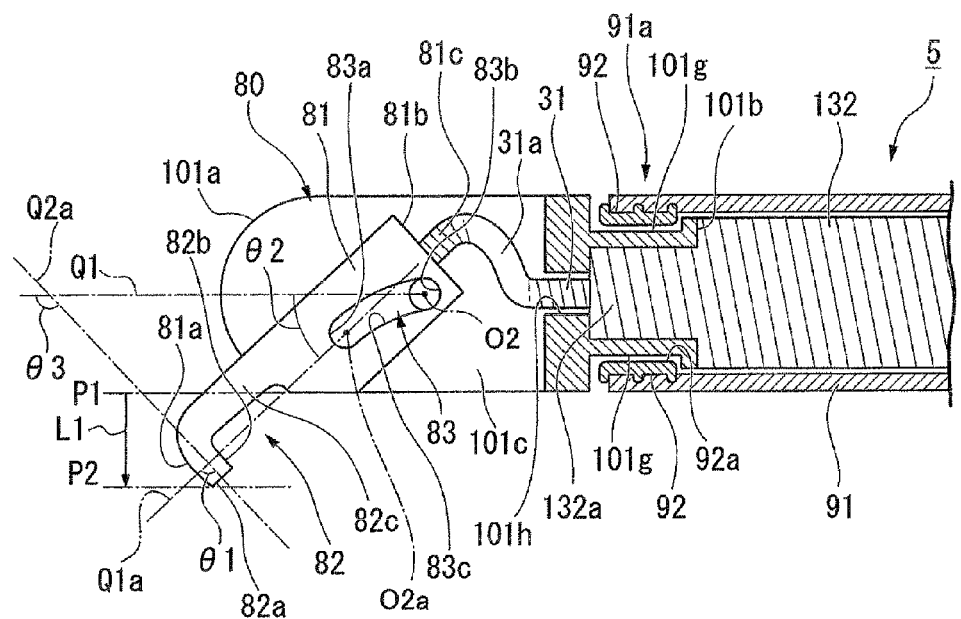
FIG. 14B is an operation-illustrating view for describing the operation of the medical device of modified example 2 at the time of use.

As shown in FIGS. 14A and 14B, in the modified example, the shape of the slit portion 83 differs from the slit of the fifth embodiment, and the slit portion 83 includes a curved portion 83c formed while curving between a distal end 83a and the proximal end 83b.

The shape of the curved portion 83c is an arc shape which extends so that the arc is separated from the fixing portion 81c toward the direction that the hook tip portion 82a of the hook portion 82 faces, as the arc proceeds to the proximal end 83b from the distal end 83a. The shape of the curved portion 83c may also be formed into a curved shape other than the arc shape.

When the medical device 5 of the modified example is used, the sliding member 37 is moved by sliding with respect to the operation body 35a in the transmission portion 100, in the same manner as described in the fifth embodiment. As a result, as shown in FIG. 14B, the operation wire 31 is drawn out to the distal end 31a side from the distal end 132a of the inner tube 132. In the incisional electrode body 81, until the regulation member 102 contacts the proximal end 83b of the slit portion 83 after the regulation member 102 performs the relative movement along the inner wall surface of the slit portion 83, the fixing portion 81c of the incisional electrode body 81 is pressed by the distal end 31a of the operation wire 31. Accordingly, the hook portion 82 provided at the distal end 81a side of the incisional electrode body 81 is drawn out to a distal end 101a side from the hook accommodating portion 101.

When the regulation member 102 contacts the proximal end 83b of the slit portion 83, the vicinity of the distal end 31a of the operation wire 31 curves so that the vicinity is projected in the direction opposite to the direction that the hook tip portion 82a faces. Moreover, taking a central axis line 02 of the regulation member 102 contacting the proximal end 83b of the slit portion 83 as a center of rotation, the incisional electrode body 81 performs the relative rotation with respect to the hook accommodating portion 101 in the direction that the hook tip portion 82a of the hook portion 82 faces.

The reason for this is that when the incisional electrode body 81 is viewed from the distal end 81a side toward the proximal end 81b side of the incisional electrode body 81, the fixing portion 81c is positioned closer to the axis portion 82c of the hook portion 82 than to the position of the proximal end 83b of the slit portion 83; therefore, the pressure acting on the fixing portion 81c acts as a moment rotating the incisional electrode body 81 around the central axis line O2 of the regulation member 102 contacting the proximal end 83b of the slit portion 83.

When the hook portion 82 rotates around the axis of the regulation member 102, the hook tip portion 82a of the hook portion 82 moves out of the radial direction by a distance L1 from a maximum external diameter portion P1 of the hook accommodating portion 101. Furthermore, at this time, the direction that the hook tip portion 82a faces is the direction of the proximal end 101b of the hook accommodating portion 101 rather than the direction that the hook tip portion 82a faces when the hook portion 82 is accommodated in the hook accommodating portion 101.

Further, the angle that the hook tip portion 82a faces with respect to a push-out direction Q1 in which the operation wire 31 is pushed out from the through-hole portion 101h is an angle θ3 obtained by adding a rotation angle θ2 of the incisional electrode body 81 to an angle θ1 formed when the incisional electrode portion 82 is accommodated in the hook accommodating portion 101. The angle θ3 is larger than the angle θ1.

Conventionally, as a medical device having a treatment portion accommodated in a treatment portion-accommodating portion provided in a distal end of an insertion portion, there is known a medical device in which the treatment portion is drawn out from the treatment portion-accommodating portion toward the push-out direction of an operation wire by performing an advancing or a retreating operation of the operation wire fixed to the treatment portion. In such a medical device, when the treatment portion contacts a treatment target site, the direction of the distal end of the insertion portion is adjusted by performing a curving operation of a curved portion of an endoscope, for example.

In the modified example, the hook portion 82 is projected from the lateral side of the hook accommodating portion 101 by the distance L1, and the angle that the hook tip portion 82a faces further increases compared to a case where the hook portion 82 is accommodated in the hook accommodating portion 101. Accordingly, even though in a space in which the angle formed between the distal end side of the insertion portion 90 of the medical device 5 and the treatment target site cannot be set so as to be large since there is not enough space in a height direction, it is possible to set the angle between the hook tip portion 82a and the treatment target sight to be large; therefore, it is possible to bring the hook portion 82 into contact with the treatment target site.

Moreover, in the modified example, since the hook portion 82 is projected outside the radial direction of the hook accommodating portion 101 by the distance L1, it is possible to bring the hook portion 82 into contact with the treatment target site even in a narrow space.

Sixth Embodiment

Figure 15A:
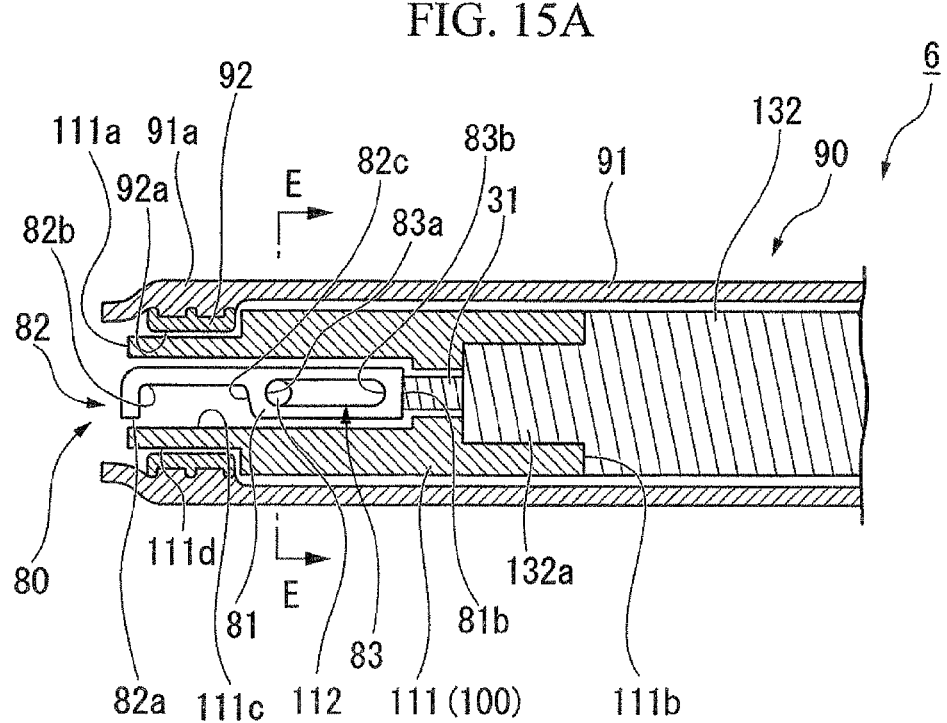
FIG. 15A is a partial cross sectional view showing a part of the configuration of a medical device of a sixth embodiment of the present invention.

Next, a medical device 6 of a sixth embodiment of the present invention will be described with reference to FIGS. 15A to 16. FIG. 15A is a cross sectional view showing a part of the configuration of the medical device 6, and FIG. 15B is a cross sectional view taken along a line E-E of FIG. 15A.

Figure 15B:
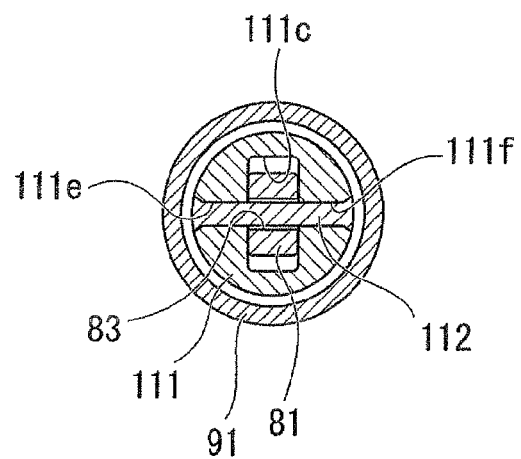
FIG. 15B is a cross sectional view taken along a line E-E of FIG. 15A.

As shown in FIGS. 15A and 15B, the configuration of the medical device 6 differs from that of the medical device 5 of the fifth embodiment in that the medical device 6 includes a hook accommodating portion 111 instead of the hook accommodating portion 101.

The hook accommodating portion 111 is formed into a substantially cylindrical shape and includes a through-hole portion 111c opened to a distal end 111a instead of the first wall portion 101c and the second wall portion 101e described in the fifth embodiment. As shown in FIG. 15B, the inner wall surface of the through-hole portion 111c is formed into a substantially rectangular shape in which the cross sectional shape thereof is orthogonal to the central axis line of the through-hole portion 111c. The incisional electrode body 81 accommodated in the through-hole portion 111c is supported by an inner wall surface facing the thickness direction of the incisional electrode body 81, among the inner wall surfaces of the through-hole portion 111c.

Further, the hook accommodating portion 111 includes a pair of through-hole portion 111e and through-hole portion 111f which is provided coaxially and wherein all the opening end portions facing each other are opened to the inner wall surface of the through-hole portion 111c. In the through-hole portions 111e and 111f, the regulation member 112 provided while penetrating the slit portion 83 of the incisional electrode body 81 is inserted and fixed, just like the regulation member 102 fixed to the hook accommodating portion 101.

Furthermore, unlike the hook accommodating portion 101, the hook accommodating portion 111 includes an engagement concave portion 111d engaging with the bearing 92 provided in the distal end 91a of the outer tube 91 in the distal end 111a side of the hook accommodating portion 111. That is, in the present embodiment, the hook accommodating portion 111 is accommodated in the outer tube 91.

Figure 16:
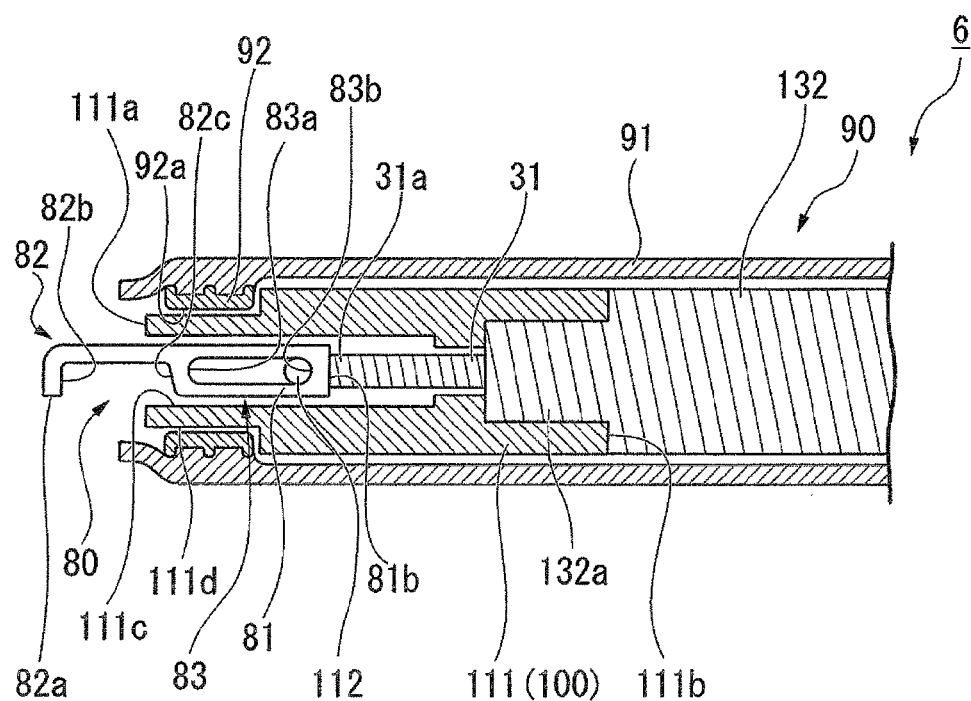
FIG. 16 is an operation-illustrating view for describing the operation of the medical device at the time of use.

FIG. 16 is an operation-illustrating view for describing the operation of the medical device 6 at the time of use. As shown in FIG. 16, in the medical device 6, when the operation wire 31 is pushed out to the distal end 31a side with respect to the inner tube 132, the hook portion 82 of the treatment portion 80 is drawn out from the through-hole portion 111c of the hook accommodating portion 111, just like the medical device 5 described in the fifth embodiment. Also, when the direction of the hook tip portion 82a of the hook portion 82 is adjusted, by rotating the operation body 35a shown in FIG. 12 relative to the outer tube 91, the inner tube 132 rotates relative to the outer tube 91 around the axis. As a result, the hook accommodating portion 111 fixed to the distal end 132a of the inner tube 132 also rotates together with the inner tube 132, and the incisional electrode body 81 supported by the through-hole portion 111c of the hook accommodating portion 111 also rotates together with the hook accommodating portion 111.

In this manner, according to the medical device 6 of the present embodiment, both the inner tube 132 and the outer tube 91 are connected to the operation body 35a just like the medical device 5 of the fifth embodiment. Therefore, when the hook portion 82 is drawn outside the hook accommodating portion 111 by sliding the sliding member 37 with respect to the operation body 35a, the outer tube 91 and the inner tube 132 do not perform the relative movement around the axis. Accordingly, the outer tube 91 and the inner tube 132 perform the relative rotation around the axis with a light force. As a result, it is possible to adjust the direction of the hook tip portion 82a of the hook portion 82 while the hook portion 82 is drawn outside the hook accommodating portion 111.

Moreover, since the hook accommodating portion 111 is accommodated in the outer tube 91, it is possible to further improve the insulation property in the distal end side of the insertion portion 90.

Hereinbefore, the embodiment of the invention has been described in detail with reference to the drawings. However, the specific configuration is not limited to the embodiment, and modifications in design or the like are also included in the invention within a range that does not depart from the scope of the invention.

For example, in the surgery for excising the lesioned mucous membrane portion H1 described in the first embodiment, the high frequency incisional devices X and Y and the medical device 1 alternatively pass thorough the treatment device channel of the endoscope. However, the invention is not limited thereto, and if a plurality of treatment device channels is provided in the endoscope, it is possible to insert the high frequency incisional devices X and Y and the medical device 1 into each treatment device channel at the same time to perform the surgery.

Further, it is not the case that the shape of the slit portion described in modified example 2 of the fifth embodiment can be applied only to the incisional electrode body including a hook portion. In incisional electrode bodies other than those with the hook portion, it is possible to achieve the same effect if the slit portion is formed to have a curved portion curving toward the side that the portion of the incisional electrode body contacting the body tissue faces, in a direction to the proximal end from the distal end of the slit portion with respect to the body tissue.

Further, in modified example 2 of the fifth embodiment, the case in which the shape of the slit portion is curved was described for example. However, the invention is not limited thereto, and the slit portion may be formed while extending between its distal end and proximal end like a straight line.

The configurational components shown in the embodiments and the modified examples can be appropriately combined.

Hereinbefore, preferable embodiments of the present invention have been described. However, the invention is not limited thereto, and addition, omission, substitution and other modification can be made on the configuration within a range that does not depart from the sprit and scope of the present invention.

Further, the invention is not limited to the above description but only to the range of the attached claims.

What is claimed is:

1. A medical device comprising:
    an insertion portion having an elongated cylindrical shape;
    a treatment portion for performing treatment in a body cavity, the treatment portion capable of protruding from and retracting into a distal end part of the insertion portion;
    an operation wire having a distal end portion fixed to the treatment portion, the operation wire provided at the insertion portion and movable along the insertion portion;
    an operation portion provided at a proximal end portion of the operation wire and configured to operate the treatment portion; and
    a protruding member protruding from an inner wall surface of the distal end part of the insertion portion and having an abutting surface facing the distal end portion of the operation wire;
    a contacting member fixed to the operation wire at a position separate from a distal end portion of the protruding member and having a contacting surface which faces the distal end portion of the operation wire; and
    a rotating bearing member mounted on the operation wire so as to be freely longitudinally slidable along an axis of the operation wire between the abutting surface of the protruding member and the contacting surface of the contacting member, a distal end of the rotating bearing member being capable of contacting the abutting surface, a proximal end of the rotating bearing member being capable of contacting the contacting surface, the rotating bearing member being freely rotatable relative to both the abutting surface and the contacting surface around the axis of the operation wire; wherein
    when the treatment portion is disposed in a position, the treatment portion protrudes from the distal end part of the insertion portion, the distal end of the rotating bearing member contacts the abutting surface and the proximal end of the rotating bearing member contacts the contacting surface.

2. The medical device according to claim 1, wherein a friction coefficient of at least one of the rotating bearing member with the protruding member and the rotating bearing member with the contacting member is smaller than a friction coefficient between the protruding member and the contacting member.

3. The medical device according to claim 1, wherein the rotating bearing member is brought into line contact or point contact with the protruding member and the contacting member.

4. The medical device according to claim 1,
    wherein the treatment portion and the operation wire are electrically conductive, and
    the operation portion includes a contact electrode portion which is capable of connecting to a high frequency power-supply device, and high frequency current is applied to the treatment portion through the operation wire.

5. The medical device according to claim 1,
    wherein the treatment portion comprises:
    a body configured to extend in an axial direction, and
    a hook portion configured to extend from the body with a tip portion facing outside a radial direction of the body.

6. The medical device according to claim 1, wherein friction coefficients of both the rotating bearing member with the protruding member and the rotating bearing member with the contacting member are smaller than a friction coefficient between the protruding member and the contacting member.

7. The medical device according to claim 2, wherein the rotating bearing member is movable relative to the operation wire in a direction of the axis of the operation wire and is rotable relative to the operation wire around the axis of the operation wire.

8. The medical device according to claim 2, wherein the treatment portion has a hooked shape so as to be capable of locking a body tissue.

* * * * *